(12) United States Patent
Nishikawa et al.

(10) Patent No.: US 11,925,443 B2
(45) Date of Patent: Mar. 12, 2024

(54) BLOOD PRESSURE MONITOR, BLOOD PRESSURE MEASUREMENT APPARATUS AND BLOOD PRESSURE MEASUREMENT METHOD

(71) Applicants: OMRON CORPORATION, Kyoto (JP); OMRON HEALTHCARE CO., LTD., Muko (JP)

(72) Inventors: Kazuyoshi Nishikawa, Ritto (JP); Shuhei Ojiro, Kyoto (JP)

(73) Assignees: OMRON CORPORATION (JP); OMRON HEALTHCARE CO., LTD. (JP)

( * ) Notice: Subject to any disclaimer, the term of this patent is extended or adjusted under 35 U.S.C. 154(b) by 1187 days.

(21) Appl. No.: 16/481,500

(22) PCT Filed: Dec. 26, 2017

(86) PCT No.: PCT/JP2017/046654
§ 371 (c)(1),
(2) Date: Jul. 29, 2019

(87) PCT Pub. No.: WO2018/179645
PCT Pub. Date: Oct. 4, 2018

(65) Prior Publication Data
US 2019/0365259 A1   Dec. 5, 2019

(30) Foreign Application Priority Data
Mar. 27, 2017 (JP) .................................. 2017-061319

(51) Int. Cl.
*A61B 5/022* (2006.01)
*A61B 5/00* (2006.01)
*A61B 5/107* (2006.01)

(52) U.S. Cl.
CPC ........ *A61B 5/02233* (2013.01); *A61B 5/1072* (2013.01); *A61B 5/681* (2013.01)

(58) Field of Classification Search
CPC ... A61B 5/02233; A61B 5/1072; A61B 5/681; A61B 5/0235; A61B 2562/0219;
(Continued)

(56) References Cited

U.S. PATENT DOCUMENTS 4,427,013 A * 1/1984 Nunn ................. A61B 5/02225
600/494
4,718,428 A * 1/1988 Russell ................ A61B 5/0235
600/490

(Continued)

FOREIGN PATENT DOCUMENTS

CN    101325907 A    12/2008
CN    202526159 U    11/2012
(Continued)

OTHER PUBLICATIONS

JPH06245911A—Sphygmomanometer—Google Patents machine translation (Year: 1993).*
(Continued)

*Primary Examiner* — Alex M Valvis
*Assistant Examiner* — Justin Xu
(74) *Attorney, Agent, or Firm* — Harness, Dickey & Pierce, P.L.C.

(57) ABSTRACT

High blood pressure measurement accuracy can be achieved with a blood pressure monitor employing a double cuff structure. A blood pressure monitor of the present invention includes a pressing member that includes a pressure cuff having a bag shape capable of containing fluid and generates a pressing force toward a measurement site of a subject when the pressing member is wound around the measurement site and the pressure cuff is inflated, and a controller
(Continued)

that controls an operation of the adjuster such that the fluid is contained in the sensing cuff in an amount corresponding to biometric information about the subject and the pressure cuff is inflated or inflated and deflated in this state when performing a blood pressure measurement, and calculates a blood pressure value of the subject based on an output from the pressure sensor.

14 Claims, 28 Drawing Sheets

(58) Field of Classification Search
CPC . A61B 5/7475; A61B 5/0205; A61B 5/02141; A61B 5/02225; A61B 5/6824; A61B 5/6831; A61B 5/1118; A61B 5/742; A61B 2562/0247; A61B 5/022; G04G 21/025
See application file for complete search history.

(56) References Cited

U.S. PATENT DOCUMENTS

| | | | |
|---|---|---|---|
| 6,336,901 B1 | 1/2002 | Itonaga et al. | |
| 8,206,310 B2 | 6/2012 | Takahashi et al. | |
| 9,820,696 B1* | 11/2017 | Narasimhan | A61B 5/7214 |
| 2006/0135873 A1* | 6/2006 | Karo | A61B 5/02233 |
| | | | 600/499 |
| 2009/0163823 A1 | 6/2009 | Takahashi et al. | |
| 2011/0160598 A1* | 6/2011 | Yamashita | A61B 5/02225 |
| | | | 600/493 |
| 2012/0302901 A1* | 11/2012 | Kobayashi | A61B 5/022 |
| | | | 600/494 |
| 2017/0202485 A1* | 7/2017 | Takasu | A61B 5/1118 |
| 2018/0085011 A1* | 3/2018 | Ma | A61B 5/02125 |

FOREIGN PATENT DOCUMENTS

| | | |
|---|---|---|
| JP | H6245911 A | 9/1994 |
| JP | H11309119 A | 11/1999 |
| JP | 2007244837 A | 9/2007 |
| JP | 201035804 A | 2/2010 |
| JP | 2010131247 A | 6/2010 |
| JP | 201261215 A | 3/2012 |
| WO | WO-2017017991 A1 | 2/2017 |

OTHER PUBLICATIONS

JPH11309119A—Cuff for sphygmomanometer—Google Patents machine translation (Year: 1998).*
WO2017017991A1—Fluid bag, fluid bag manufacturing method, and cuff for measuring blood pressure—Google Patents machine translation (Year: 2016).*
Chinese Office Action dated Jun. 28, 2021 for Application No. 201780085994.3 (with English translation) (19 pages).
International Search Report (in English and Japanese) and Written Opinion (in Japanese) issued in PCT/JP2017/046654, dated Mar. 6, 2018; ISA/JP.
International Preliminary Report on Patentability for PCT/JP2017/046654, dated Oct. 1, 2019 (10 pages).
Office Action for Japanese Application No. 2017-061319 dated Jul. 21, 2020 (with English translation) (6 pages).

* cited by examiner

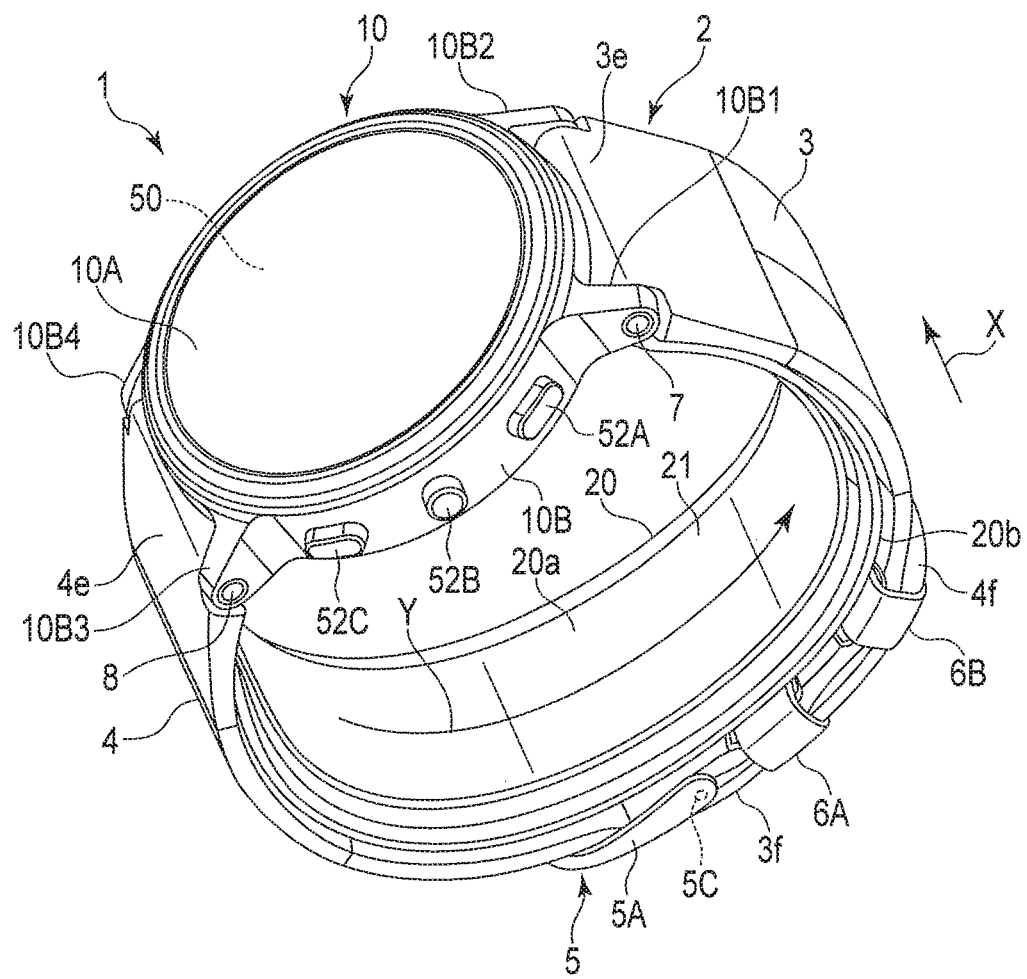
F I G. 1

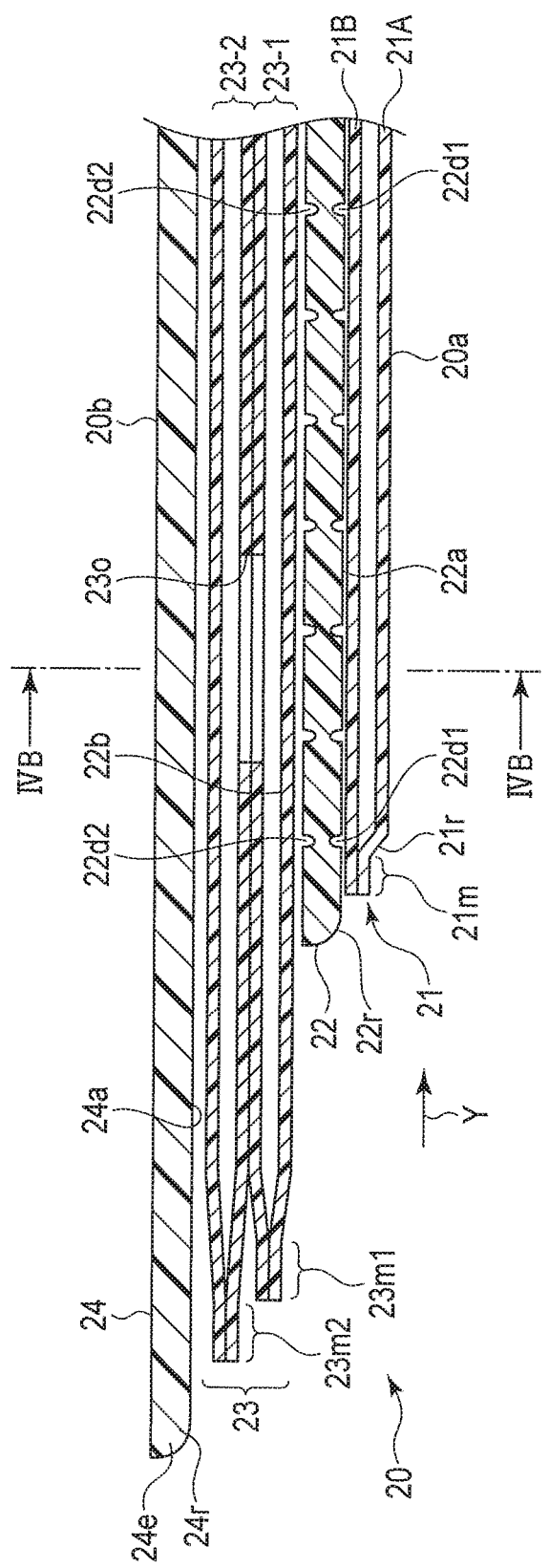
F I G. 4A

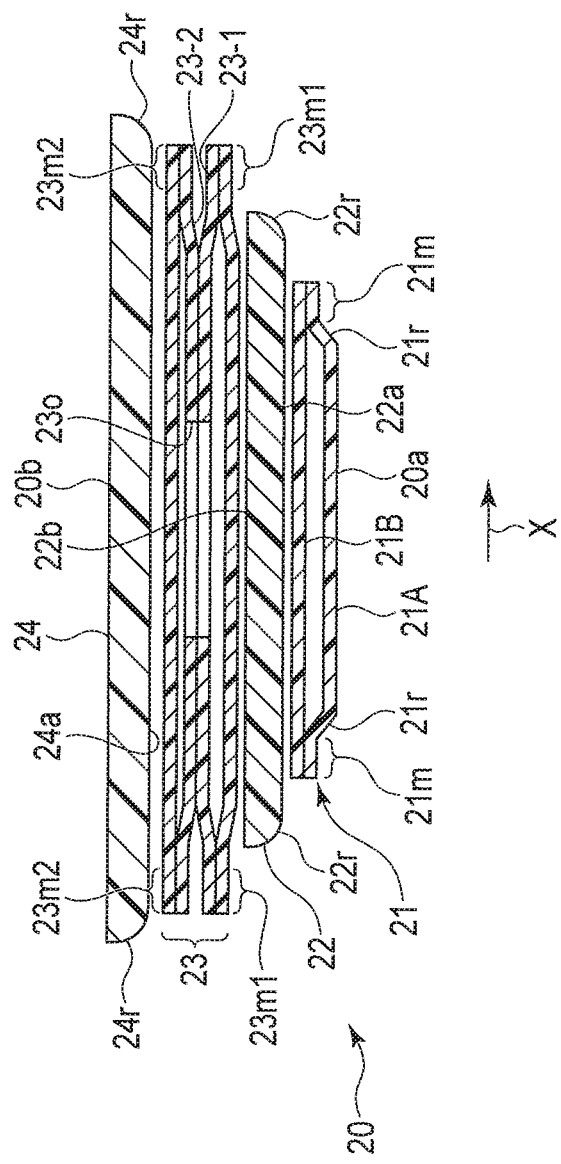
F I G. 4B

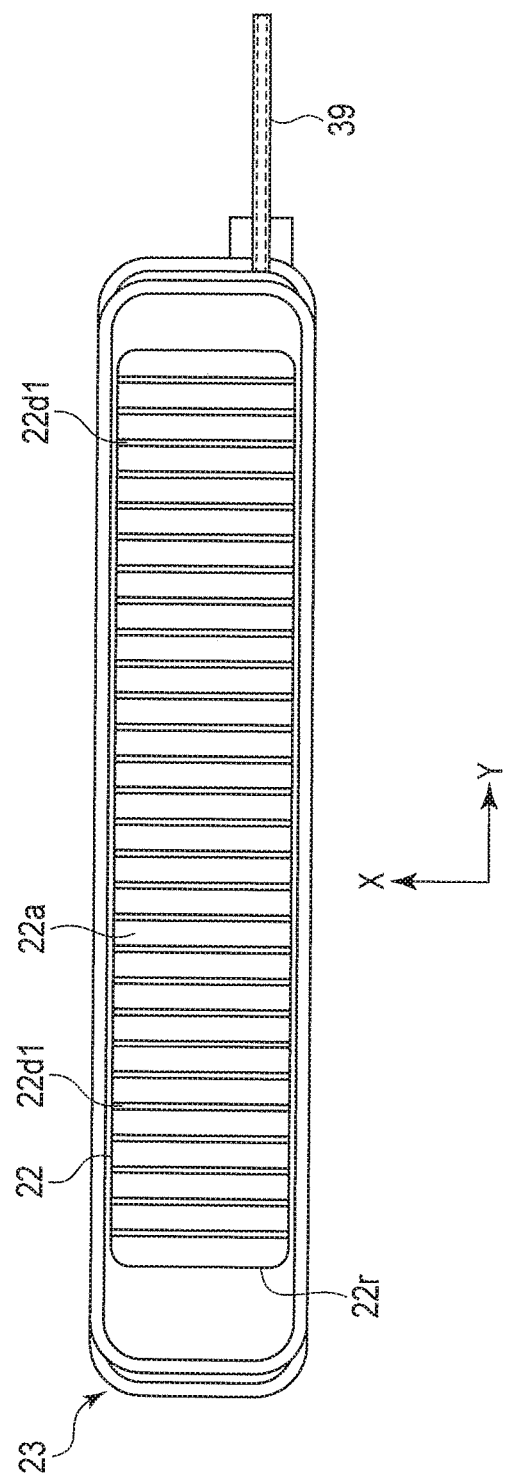
F I G. 5B

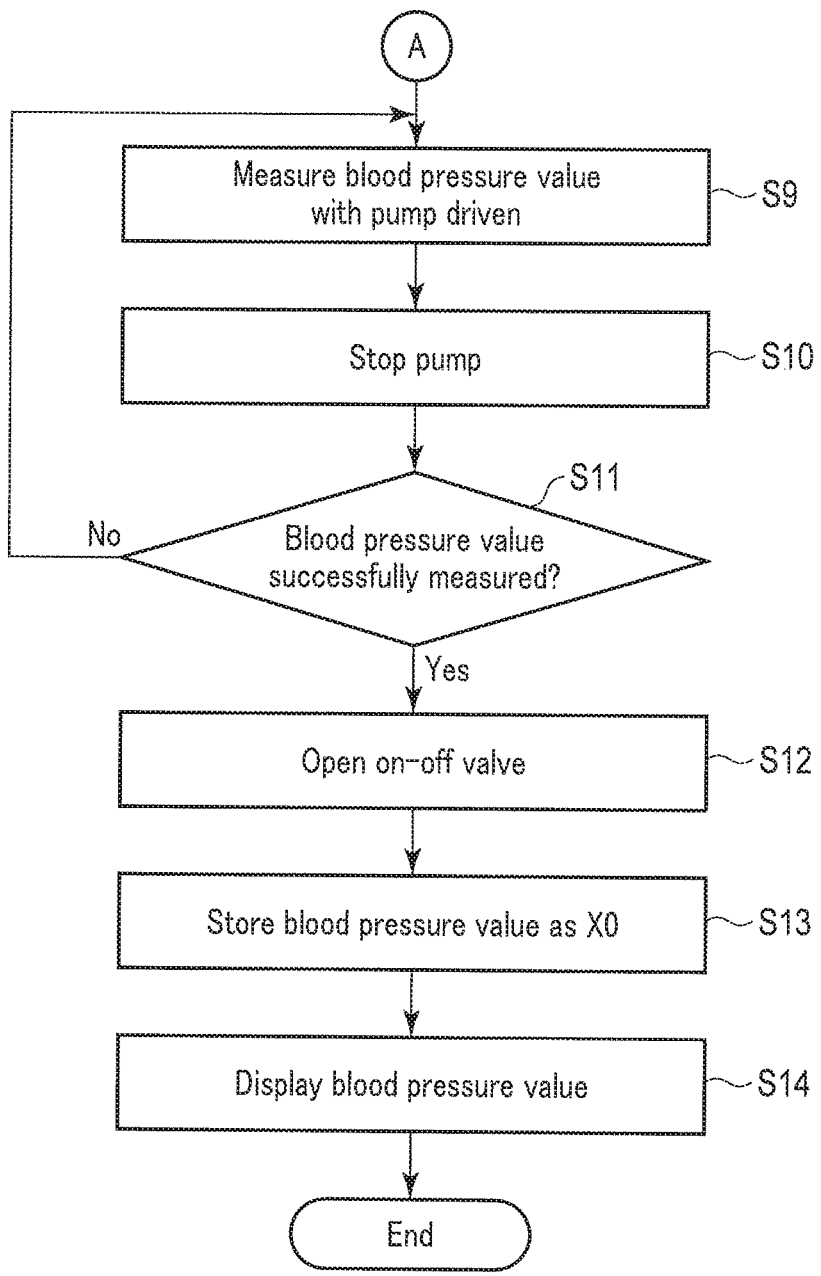
F I G. 12

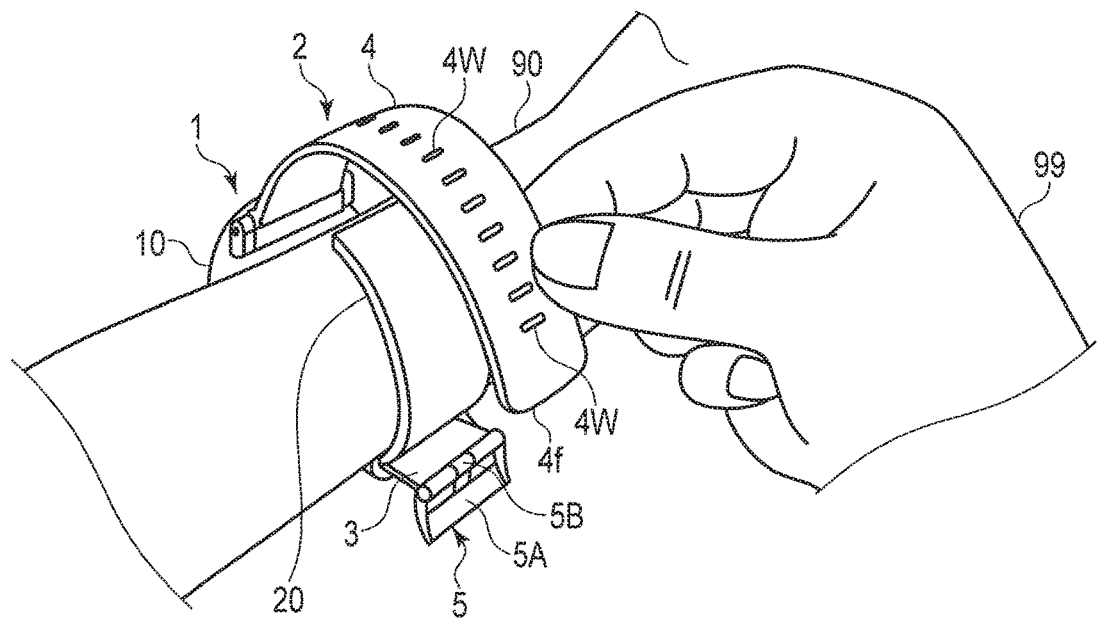
F I G. 13B
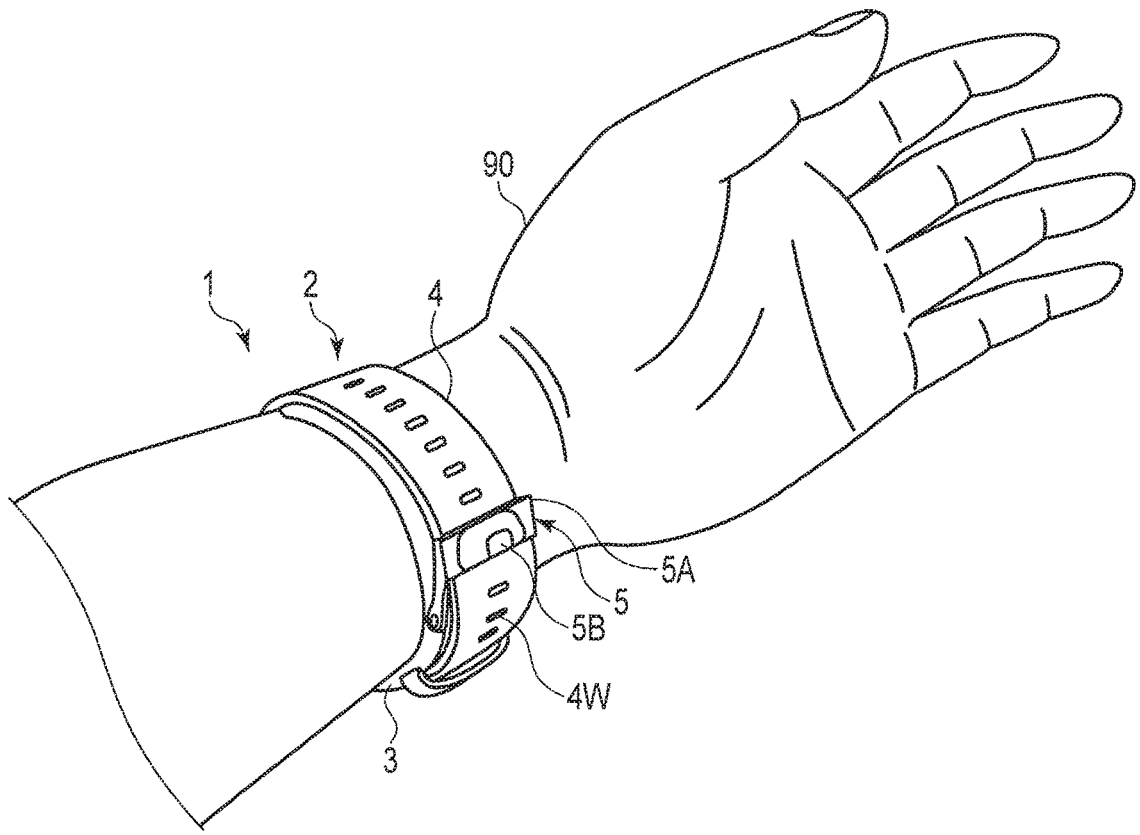
F I G. 13C

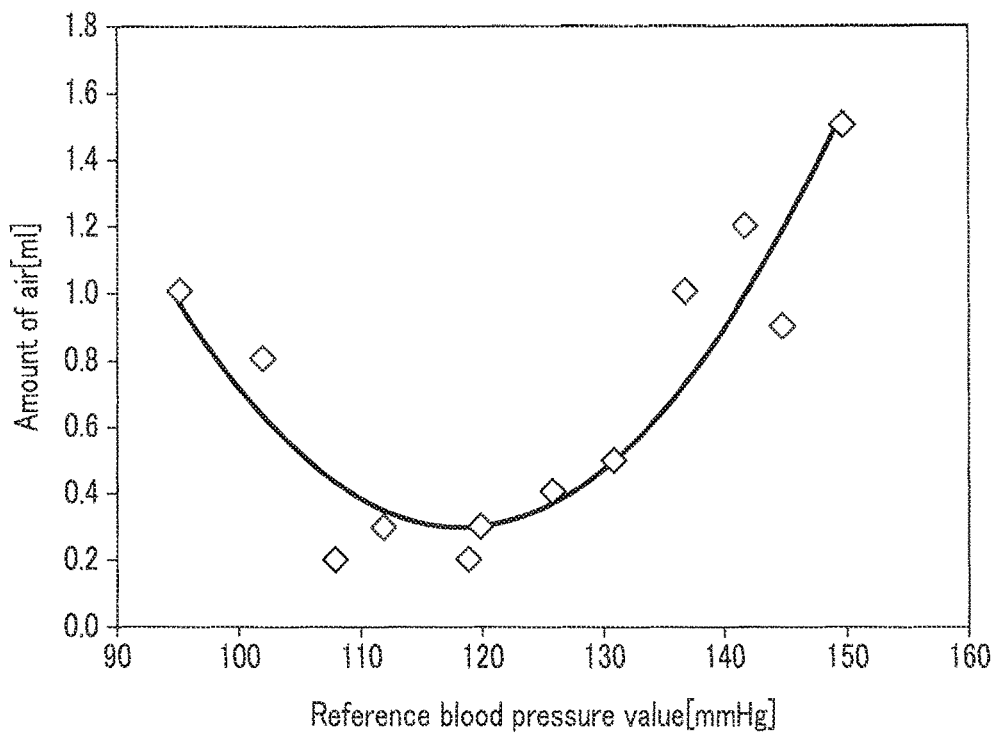
F I G. 24
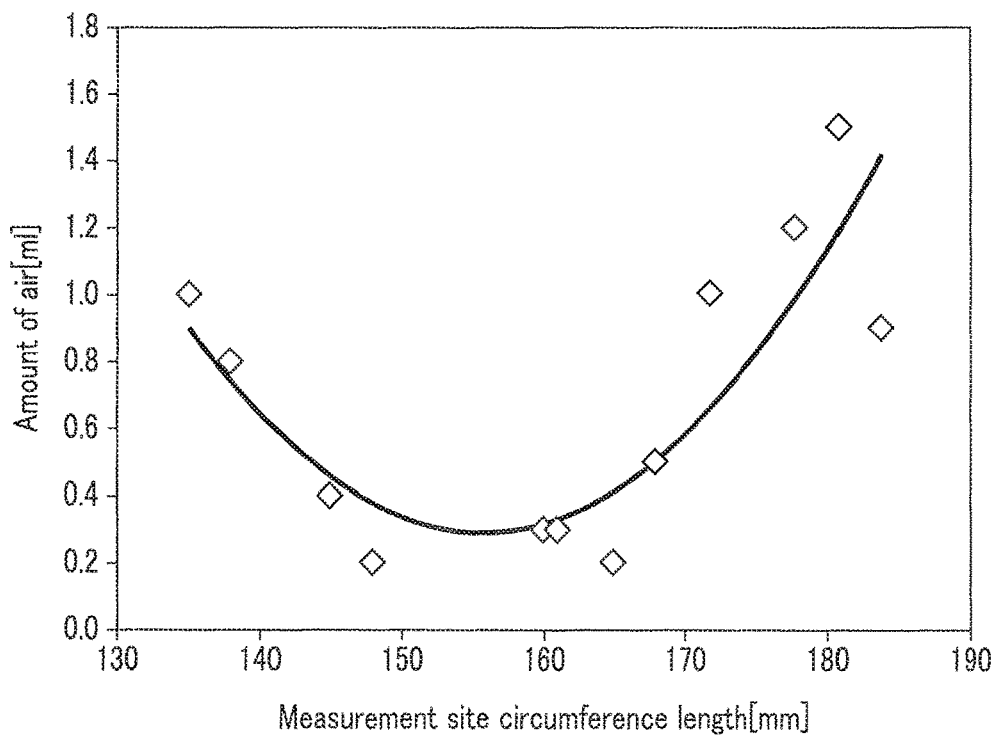
F I G. 25

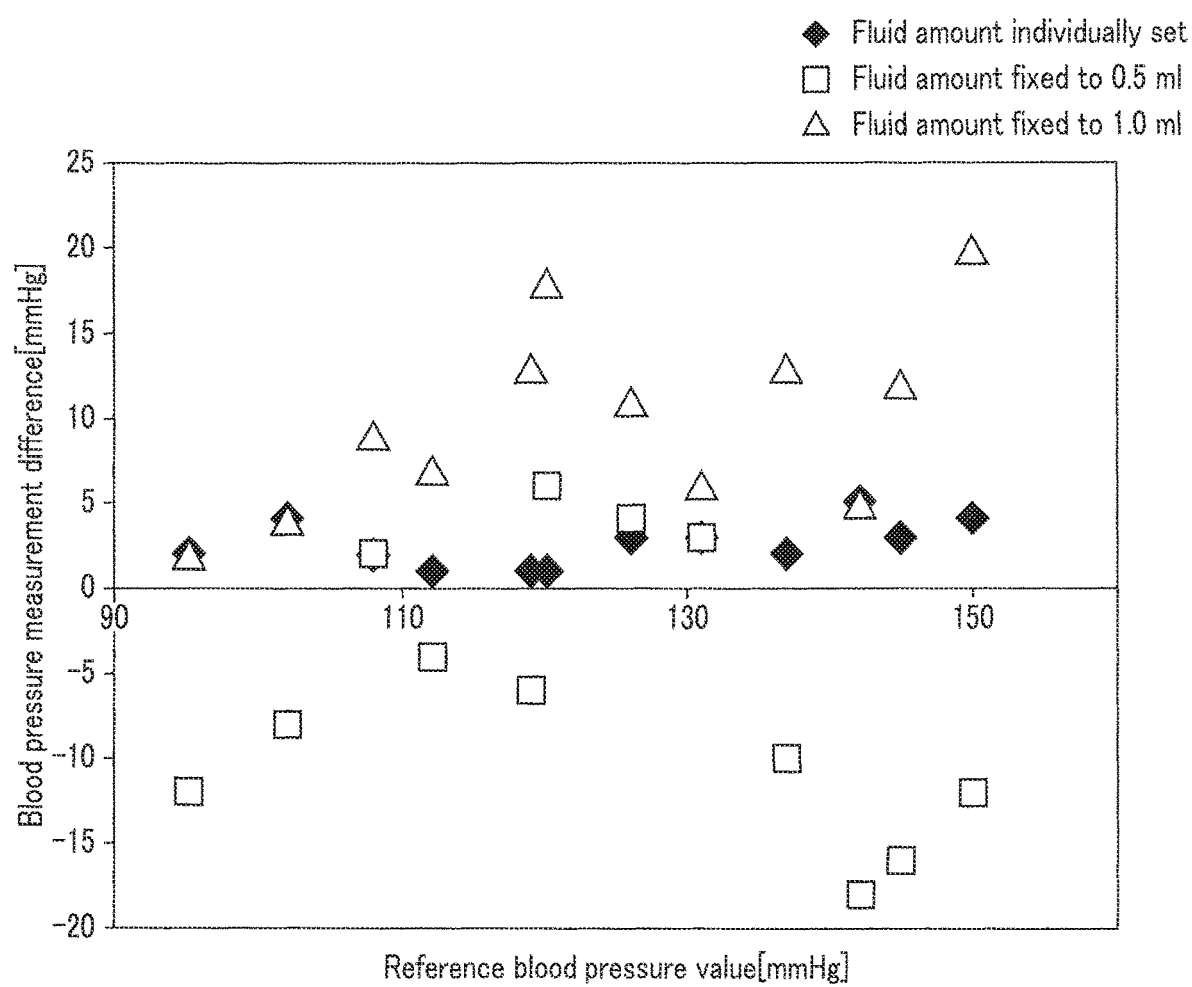
F I G. 26

BLOOD PRESSURE MONITOR, BLOOD PRESSURE MEASUREMENT APPARATUS AND BLOOD PRESSURE MEASUREMENT METHOD

CROSS-REFERENCE TO RELATED APPLICATIONS

This is a U.S. National Phase Application under 35 U.S.C. 371 of International Application No. PCT/JP2017/046654 (not published in English), filed Dec. 26, 2017, which claims priority to Japanese Patent Application No. 2017-061319, filed Mar. 27, 2017. The disclosures of the above applications are incorporated herein by reference.

FIELD

The present invention relates to a blood pressure monitor, a blood pressure measurement apparatus, and a blood pressure measurement method.

BACKGROUND

Jpn. Pat. Appln. KOKAI Publication No. 11-309119 discloses an example of a blood pressure monitor that is a wrist blood pressure monitor including a pressurization fluid bag (sensing cuff) and a pressing fluid bag (pressure cuff). This blood pressure monitor has a structure in which the pressurization fluid bag, a curler, which is a plate member having an appropriate level of elasticity, and the pressing fluid bag are fixed to a wrist using a band (belt) such that they are stacked in this order from the wrist side when performing blood pressure measurement.

When performing blood pressure measurement using this blood pressure monitor, a predetermined amount of fluid is supplied to the pressurization fluid bag after fixing the monitor to the wrist using the band, or the predetermined amount of fluid is sealed therein in advance. Next, the pressing fluid bag is supplied with fluid to be sufficiently inflated. Then, the fluid is gradually discharged from the pressing fluid bag, and a pressure sensor detects a pressure change occurring in the pressurization fluid bag in this depressurization process. Finally, a blood pressure value is calculated from an output from this pressure sensor.

In this blood pressure monitor, as described above, a predetermined amount of air is supplied to the blood pressure measurement cuff or a predetermined amount of fluid is sealed therein in advance. The force for sufficiently compressing a part of a living body is obtained by inflating the pressing fluid bag. Thus, the blood pressure monitor can be mounted without a feeling of being oppressed, discomfort, or the like.

SUMMARY

The present inventors have found that in a blood pressure monitor employing a so-called double cuff structure in which the sensing cuff and the pressure cuff are stacked in this order from a measurement site when performing blood pressure measurement, the measurement results varies among individuals.

In view of this, an object of the present invention is to achieve high blood pressure measurement accuracy with a blood pressure monitor employing a double cuff structure.

According to a first aspect of the present invention, there is provided a blood pressure monitor comprising: a pressing member that includes a pressure cuff having a bag shape capable of containing a first fluid and generates a pressing force toward a measurement site of a subject when the pressing member is wound around the measurement site and the pressure cuff is inflated; a sensing cuff having a bag shape capable of containing a second fluid and provided on a facing surface of the pressing member that faces the measurement site; an adjuster that adjusts an amount of the first fluid in the pressure cuff and an amount of the second fluid in the sensing cuff; a pressure sensor that detects pressure in the sensing cuff; and a controller that controls an operation of the adjuster such that the second fluid is contained in the sensing cuff in an amount corresponding to biometric information about the subject and the pressure cuff is inflated or inflated and deflated in this state when performing a blood pressure measurement, and calculates a blood pressure value of the subject based on an output from the pressure sensor.

According to a second aspect of the present invention, there is provided the blood pressure monitor according to the first aspect, further comprising an input unit for inputting information, wherein the controller controls the operation of the adjuster using at least part of the information input through the input unit, as the biometric information, and calculates the blood pressure value of the subject based on the output from the pressure sensor.

According to a third aspect of the present invention, there is provided the blood pressure monitor according to the first aspect, further comprising an input unit used for inputting information, wherein the controller is capable of switching a measurement mode from a first mode to a second mode, when blood pressure measurement is performed in the first mode, the controller controls the operation of the adjuster using, as the biometric information, at least part of the information input through the input unit and calculates the blood pressure value of the subject based on the output from the pressure sensor, and when the blood pressure measurement is performed in the second mode, the controller controls the operation of the adjuster using, as the biometric information, the blood pressure value calculated by the controller in the blood pressure measurement previously performed, and calculates the blood pressure value of the subject based on the output from the pressure sensor.

According to a fourth aspect of the present invention, there is provided the blood pressure monitor according to the third aspect, wherein the controller repeats the blood pressure measurement in the second mode until variation in the blood pressure value calculated falls within a tolerable range.

According to a fifth aspect of the present invention, there is provided the blood pressure monitor according to any one of the second to fourth aspects, wherein the information input through the input unit includes at least one of a blood pressure of the subject and a circumference length of the measurement site.

According to a sixth aspect of the present invention, there is provided the blood pressure monitor according to the first aspect, wherein the controller repeats blood pressure measurement until variation in the blood pressure calculated falls within a tolerable range, and in the blood pressure measurement performed for second time and after, controls an amount of the second fluid supplied to the sensing cuff by the adjuster using, as the biometric information, the blood pressure value calculated by the controller in the blood pressure measurement previously performed.

According to a seventh aspect of the present invention, there is provided the blood pressure monitor according to any one of the first to sixth aspects, wherein the sensing cuff includes a first sheet facing the facing surface, and a second sheet positioned between the first sheet and the facing surface, and the sensing cuff in a natural state with one of the first sheet and the second sheet being flat has a slack in the other of the first sheet and the second sheet, the slack extending along a longitudinal direction of the sensing cuff between edges on both ends in a width direction of the sensing cuff.

According to an eighth aspect of the present invention, there is provided the blood pressure monitor according to any one of the first to seventh, wherein the pressing member further includes a belt that is provided to face an outer circumference surface of the pressure cuff and is wound around the measurement site, and a back plate that is provided between the pressure cuff and the sensing cuff, and extends along a circumference direction of the measurement site.

According to a ninth aspect of the present invention, there is provided the blood pressure monitor according to any one of the first to eighth, wherein the sensing cuff has a Shore A hardness of 60 or less.

Here, the Shore A hardness is a durometer hardness obtained by a type A durometer hardness test defined in JIS K6253-3: 2012 ("Rubber, vulcanized or thermoplastic—Determination of hardness—. Part 3: Durometer method").

According to a tenth aspect of the present invention, there is provided a blood pressure measurement apparatus comprising: a pressing member that includes a pressure cuff having a bag shape capable of containing a first fluid and generates pressing force toward a measurement site of a subject when the pressing member is wound around the measurement site and the pressure cuff is inflated; a sensing cuff having a bag shape capable of containing a second fluid and provided on a facing surface of the pressing member that faces the measurement site; an adjuster that adjusts an amount of the first fluid in the pressure cuff and an amount of the second fluid in the sensing cuff; a pressure sensor that detects pressure in the sensing cuff; and a controller that controls an operation of the adjuster such that the second fluid is contained in the sensing cuff in an amount corresponding to biometric information about the subject and the pressure cuff is inflated or inflated and deflated in this state when performing a blood pressure measurement, and calculates a blood pressure value of the subject based on an output from the pressure sensor.

According to an eleventh aspect of the present invention, there is provided a blood pressure measurement method comprising: winding a pressing member and a sensing cuff around a measurement site of a subject, wherein the pressing member includes a pressure cuff having a bag shape capable of containing a first fluid and generates pressing force toward the measurement site when the pressing member is wound around the measurement site and the pressure cuff is inflated, and the sensing cuff has a bag shape capable of containing a second fluid and is provided on a facing surface of the pressing member that faces the measurement site; and containing the second fluid in the sensing cuff in an amount corresponding to biometric information about the subject, inflating or inflating and deflating the pressure cuff in this state, and obtaining a blood pressure value of the subject based on pressure in the sensing cuff, with the pressure cuff inflated or inflated and deflated in a state that the second fluid in an amount corresponding to biometric information about the subject is contained in the sensing cuff.

As described above, the present inventors have found that the measurement results obtained by blood pressure monitor employing the double cuff structure vary among individuals. Specifically, a blood pressure monitor employing the double cuff structure that achieves sufficiently high blood pressure measurement accuracy for one subject, may fail to achieve high blood pressure measurement accuracy for other subjects.

The present inventors investigated the reason for this and found out the following facts. Specifically, the blood pressure measurement accuracy is affected by biometric information about a subject including a blood pressure value and the circumference length of a measurement site, as well as the tension on the sensing cuff. Variations in the blood pressure value of the subject and the circumference length of the measurement site result in variations in a range of tension on the sensing cuff within which high blood pressure measurement accuracy may be achieved.

In view of the above, the present inventors have found that setting the tension on the sensing cuff at the time of blood pressure measurement to a value according to the biometric information about the subject can achieve high blood pressure measurement accuracy.

Unfortunately, it is difficult to provide the blood pressure monitor with a capability of measuring the tension on the sensing cuff. Still, the amount of fluid supplied to the sensing cuff, which is a parameter related to the tension on the sensing cuff, can be relatively easily obtained based on, for example, time period during which the fluid is supplied to the sensing cuff and pressure in the sensing cuff after the fluid has been supplied to the sensing cuff and before the measurement starts.

Thus, setting the amount of the fluid in the sensing cuff at the time of blood pressure measurement to a value according to the biometric information about the subject can achieve high blood pressure measurement accuracy. Therefore, the blood pressure monitor according to the first aspect of the present invention employing the double cuff structure can achieve high blood pressure measurement accuracy.

Regarding the fact that the variation in the blood pressure value of the subject and the circumference length of the measurement site result in variations in a range of amounts of fluid supplied to the sensing cuff within which high blood pressure measurement accuracy may be achieved, the inventors of the present invention believes the reason as follows.

The positions of the arteries and bones and the amount of fat at the measurement site of the subject, which is the wrist, the ankle, or the upper arm for example, vary among individuals. Furthermore, the blood pressure value of the subject also varies among individuals. The differences in the position of the artery and bone, the amount of fat, and the blood pressure value, leads to differences in how the pulse wave signal is transmitted, making it difficult to achieve high blood pressure measurement accuracy. The height, the weight, the body fat percentage, the circumference length of the measurement site, and the like are somewhat correlated with the positions of the artery and bone and the amount of fat. Therefore, setting the amount of fluid in the sensing cuff when performing blood pressure measurement to an amount that varies according to biometric information such as blood pressure value, height, body weight, body fat percentage, and circumference length of the measurement site, can achieve high blood pressure measurement.

The blood pressure monitor according to the second aspect of the present invention is the blood pressure monitor according to the first aspect further including an input unit used for inputting information, in which the controller controls the operation of the adjuster using at least part of the information input through the input unit, as the biometric information, and calculates the blood pressure value of the subject based on the output from the pressure sensor. This blood pressure monitor uses biometric information known in advance, and thus can achieve high blood pressure measurement accuracy from the first blood pressure measurement.

The blood pressure monitor according to the third aspect of the present invention is the blood pressure monitor according to the first aspect further including an input unit used for inputting information, in which the controller is capable of switching a measurement mode from a first mode to a second mode, when blood pressure measurement is performed in the first mode, the controller controls the operation of the adjuster using at least part of the information input through the input unit, as the biometric information, and calculates the blood pressure value of the subject based on the output from the pressure sensor, and when the blood pressure measurement is performed in the second mode, the controller controls the operation of the adjuster using, as the biometric information, the blood pressure value calculated by the controller in the blood pressure measurement previously performed, and calculates the blood pressure value of the subject based on the output from the pressure sensor. Thus, when the measurement is performed, for example, in the second mode, high blood pressure measurement accuracy can always be achieved even if the blood pressure value of the subject gradually changes.

The blood pressure monitor according to the fourth aspect of the present invention is the blood pressure monitor according to the third aspect, in which the controller repeats the blood pressure measurement in the second mode until variation in the blood pressure value calculated falls within a tolerable range. Thus, with the blood pressure monitor, high blood pressure measurement accuracy can be achieved even when the blood pressure value largely fluctuates in a short period of time.

The blood pressure monitor according to the fifth aspect of the present invention is the blood pressure monitor according to any one of the second to the fourth aspects, in which the information input through the input unit includes at least one of a blood pressure of the subject and a circumference length of the measurement site. The blood pressure of the subject and the circumference length of the measurement site are biometric information that can be easily obtained, and can be used for achieving particularly high blood pressure measurement accuracy.

The blood pressure monitor according to the sixth aspect of the present invention is the blood pressure monitor according to the first aspect in which the controller repeats blood pressure measurement until variation in the blood pressure calculated falls within a tolerable range, and in the blood pressure measurement performed for second time and after, controls an amount of the second fluid supplied to the sensing cuff by the fluid supplying apparatus using, as the biometric information, the blood pressure value calculated by the controller in the blood pressure measurement previously performed. This blood pressure monitor can achieve high blood pressure measurement accuracy, for example, without requiring the subject to input the biometric information. Furthermore, with the blood pressure monitor, high blood pressure measurement accuracy can be achieved even when the blood pressure value largely fluctuates in a short period of time.

The blood pressure monitor according to the seventh aspect of the present invention is the blood pressure monitor according to any one of the first to the sixth aspects, in which the sensing cuff includes a first sheet facing the facing surface, and a second sheet positioned between the first sheet and the facing surface, the sensing cuff in a natural state with one of the first sheet and the second sheet being flat has a slack in the other of the first sheet and the second sheet, and the slack extends along a longitudinal direction of the sensing cuff between edges on both ends in a width direction of the sensing cuff. With this slack, a gap extending in the longitudinal direction is produced in the sensing cuff at the time of blood pressure measurement. Through the gap, flow of the second fluid, transmission of the pulse wave signal, and the like can be implemented. Thus, high blood pressure measurement accuracy can be achieved even when the amount of the second fluid in the sensing cuff is small.

The blood pressure monitor according to the eighth aspect of the present invention is the blood pressure monitor according to any one of the first to the seventh aspects, in which the pressing member further includes a belt that is provided to face an outer circumference surface of the pressure cuff and is wound around the measurement site, and a back plate that is provided between the pressure cuff and the sensing cuff, and extends along a circumference direction of the measurement site. With the belt and the back plate, pressurization can be more uniformly performed. Thus, with this blood pressure monitor, particularly high blood pressure measurement accuracy can be achieved.

The blood pressure monitor according to the ninth aspect of the present invention is the blood pressure monitor according to any one of the first to the eighth aspects, in which the sensing cuff has a Shore A hardness of 60 or less. Such sensing cuff involves a smaller change in tension due to variation of the amount of second fluid supplied thereto. Thus, with such a blood pressure monitor, the tension thereof can be set more finely, and therefore, blood pressure measurement with high accuracy can be achieved easily.

The blood pressure measurement apparatus according to the tenth aspect of the present invention includes the components of the blood pressure monitor according to the first aspect. This "blood pressure measurement apparatus" is an apparatus having a blood pressure measurement function, is preferably an apparatus having the blood pressure measurement function and other functions, examples of which include a wristwatch-type wearable device such as a smart watch. The blood pressure measurement apparatus includes the components of the blood pressure monitor according to the first aspect, and thus employs the double cuff structure but can still achieve high blood pressure measurement accuracy.

The blood pressure measurement method according to the eleventh aspect of the present invention includes winding a pressing member and a sensing cuff around a measurement site of a subject, in which the pressing member includes a pressure cuff having a bag shape capable of containing a first fluid and generates pressing force toward the measurement site when the pressing member is wound around the measurement site and the pressure cuff is inflated, and the sensing cuff has a bag shape capable of containing a second fluid and is provided on a facing surface of the pressing member that faces the measurement site, and containing the second fluid in the sensing cuff in an amount corresponding to biometric information about the subject, inflating or inflating and deflating the pressure cuff in this state, and obtaining a blood pressure value of the subject based on pressure in the sensing cuff. Thus, with the blood pressure method, it is possible to achieve high blood pressure measurement accuracy using a double cuff structure.

BRIEF DESCRIPTION OF THE DRAWINGS

FIG. 1 is a perspective view of a blood pressure monitor according to an embodiment of the present invention, in a state where a belt is fastened;

FIG. 4A is an enlarged cross-sectional view of a part of FIG. 3B;

FIG. 4B is a cross-sectional view of the structure illustrated in FIG. 4A, taken along line IVB-IVB;

FIG. 5B is a plan view of the back plate of the cuff structure illustrated in FIGS. 3A and 3B;

FIG. 12 is a flowchart showing the remaining steps of the blood pressure measurement method the some steps of which are illustrated in FIG. 11;

FIG. 13B is a perspective view illustrating how the subject fixes the blood pressure monitor illustrated in FIGS. 1 and 2 to the left wrist;

FIG. 13C is a perspective view illustrating how the blood pressure monitor illustrated in FIGS. 1 and 2 is mounted on the left wrist of the subject;

FIG. 24 is a graph showing an example of the relationship between the reference blood pressure value and the amount of air in the sensing cuff;

FIG. 25 is a graph showing an example of the relationship between the circumference length of the measurement site and the amount of air in the sensing cuff; and FIG. 26 is a graph illustrating an example of a blood pressure measurement error in a case that an amount of air in the sensing cuff is fixed and a blood pressure measurement error in a case that the amount of air in the sensing cuff is individually set.

DETAILED DESCRIPTION

Figure 2:
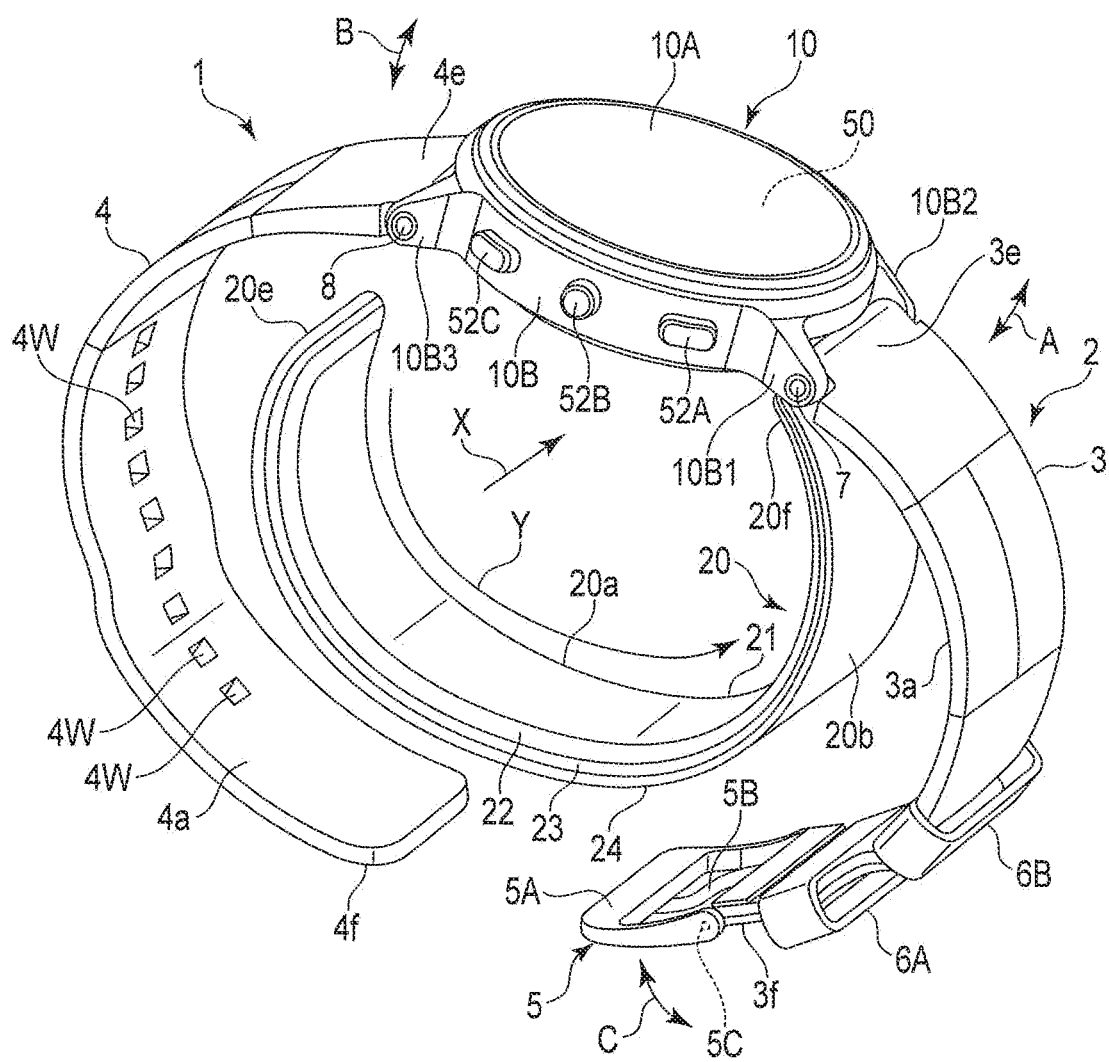
FIG. 2 is a perspective view of the blood pressure monitor of FIG. 1 in a state where the belt is released.

Hereinafter, embodiments of the present invention will be described with reference to the drawings. Elements having the same or similar functions are denoted by the same reference numerals, and redundant explanations will be omitted.

Configuration of Blood Pressure Monitor

FIG. 1 is a perspective view of a blood pressure monitor according to an embodiment of the present invention, in a state where a belt is fastened. FIG. 2 is a perspective view of the blood pressure monitor of FIG. 1 in a state where the belt is released.

The blood pressure monitor 1 illustrated in FIGS. 1 and 2 is a blood pressure monitor of a wristwatch type having functions of an activity meter, a pulsimeter, and the like. Thus, the blood pressure monitor 1 is a wristwatch type wearable device.

The blood pressure monitor 1 includes a main body 10, a belt 2 and a cuff structure 20.

The main body 10 is formed to be small and thin so as not to interfere with the daily activities of a subject (user).

In this example, the main body 10 includes a case 10B having a substantially short-cylindrical shape, a circular glass plate 10A attached to one opening (upper opening in FIGS. 1 and 2) of the case 10B, and a back cover 10C (see FIG. 6) attached to the other opening of the case 10B. In the following description on the main body 10, the glass plate 10A side and the back cover 10C side are referred to as a front surface side and a back surface side, respectively.

The case 10B has a side surface provided with rugs 10B1, 10B2, 10B3 and 10B4 for attaching the belt 2. The rugs 10B1 and 10B2 protrude in one direction from the side surface of the substantially short-cylindrical portion of the case 10B, and are provided with coaxial through holes. Further, the rugs 10B3 and 10B4 protrude from the side surface of the substantially short-cylindrical portion of the case 10B in the direction substantially opposite to that of the rugs 10B1 and 10B2, and are also provided with coaxial through holes.

A display 50 is installed in the case 10B and on the back surface side of the glass plate 10A. The display 50 is a liquid crystal display in this example, and displays, for example, information about blood pressure measurement such as a blood pressure measurement result. The display 50 is not limited to a liquid crystal display, and may be another type of display such as an organic electroluminescence (EL) display, for example. Furthermore, the display 50 may include a light emitting diode.

In the main body 10, push-type switches 52A to 52C are provided at positions on a side surface of the case 10B between the rugs 10B1 and 10B3. The switches 52A to 52C form an operation unit that is an example of an input unit. The input unit will be described in detail later.

The main body 10 incorporates therein a blood pressure measurement element including a pump. The blood pressure measurement element will also be described in detail later.

The belt 2 extends from the main body 10 and is wound around a measurement site, which is the left wrist in this example, for mounting. The length of the belt 2 in a width direction X is set to be 29 mm in this example. The thickness of the belt 2 is set to be 2 mm in this example.

As is clear in FIG. 2, the belt 2 includes a first belt portion 3 extending from the position on the main body 10 at the rugs 10B1 and 10B2 and a second belt portion 4 extending from the position on the main body 10 at the rugs 10B3 and 10B4 in a direction opposite to that of the first belt portion 3. The first belt portion 3 has, in the vicinity of the main body 10, a base portion 3e that is attached to the rugs 10B1 and 10B2 of the main body 10 via a connecting bar 7 (a spring bar, for example) extending in the width direction X of the belt such that it can pivot in the directions indicated by a double-headed arrow A. Similarly, the second belt portion 4 has, in the vicinity of the main body 10, a base portion 4e that is attached to the rugs 10B3 and 10B4 of the main body 10 via a connecting bar 8 (a spring bar, for example) extending in the width direction X of the belt such that it can pivot in directions indicated by a double-headed arrow B.

A buckle 5 is attached to a distal end portion 3f of the first belt portion 3, which is far from the main body 10. The buckle 5 is of a known type and includes a substantially U-shaped frame 5A, a tongue 5B, and a connecting bar 5C extending in the width direction X of the belt. Each of the frame 5A and the tongue 5B is attached via the connecting bar 5C to the distal end portion 3f of the first belt portion 3, which is far from the main body 10, to be able to pivot in the directions indicated by a double-headed arrow C. A portion of the first belt portion 3 between the distal end portion 3f and the base portion 3e includes a ring-shaped belt holders 6A and 6B integrally provided at predetermined positions in a longitudinal direction (corresponding to a circumference direction Y of a left wrist 90) of the first belt portion 3. An inner circumference surface 3a of the first belt portion 3 does not protrude at the positions of the belt holders 6A and 6B, whereby the belt 2 uniformly surrounds and holds the cuff structure 20.

A plurality of small holes 4w are formed in a portion of the second belt portion 4 between the base portion 4e and the distal end portion 4f far from the main body 10 such that the holes 4w extend through the second belt portion 4 in the thickness direction. When the first belt portion 3 and the second belt portion 4 are fastened to each other, the distal end portion 4f of the second belt portion 4 and the portion continuous thereto are inserted into the opening of the frame 5A of the buckle 5, and the tongue 5B of the buckle 5 is inserted to any one of the plurality of small holes 4w of the second belt portion 4. In this manner, the first belt portion 3 and the second belt portion 4 are fastened as illustrated in FIG. 1.

In this example, the first belt portion 3 and the second belt portion 4 forming the belt 2 are made of a plastic material that is flexible in the thickness direction and is substantially non-elastic in the longitudinal direction (corresponding to the circumference direction Y of the left wrist 90). Thus, the belt 2 can be easily wound around and hold the outer circumference side of the cuff structure 20 when mounting, and can assist the compression of the left wrist 90 at the time of blood pressure measurement described later. The first belt portion 3 and the second belt portion 4 may be made of a leather material. Furthermore, the frame 5A and the tongue 5B forming the buckle 5, which are made of a metal material in this example, may also be made of a plastic material.

The cuff structure 20 has a strip shape, and has one end 20f attached to the main body 10 as illustrated in FIG. 2. The cuff structure 20 includes a curler 24 provided at the outermost circumference, a pressure cuff 23 installed along the inner circumference surface of the curler 24, a back plate 22 serving as a reinforcing plate installed along the inner circumference surface of the pressure cuff 23, and a sensing cuff 21 provided along the inner circumference surface of the back plate 22. In the present embodiment, the belt 2 described above, the curler 24, the pressure cuff 23, and the back plate together function as a pressing member capable of generating pressing force toward the wrist. This pressing member compresses the wrist via the sensing cuff 21.

The cuff structure is described in more detail below.

Figure 3A:
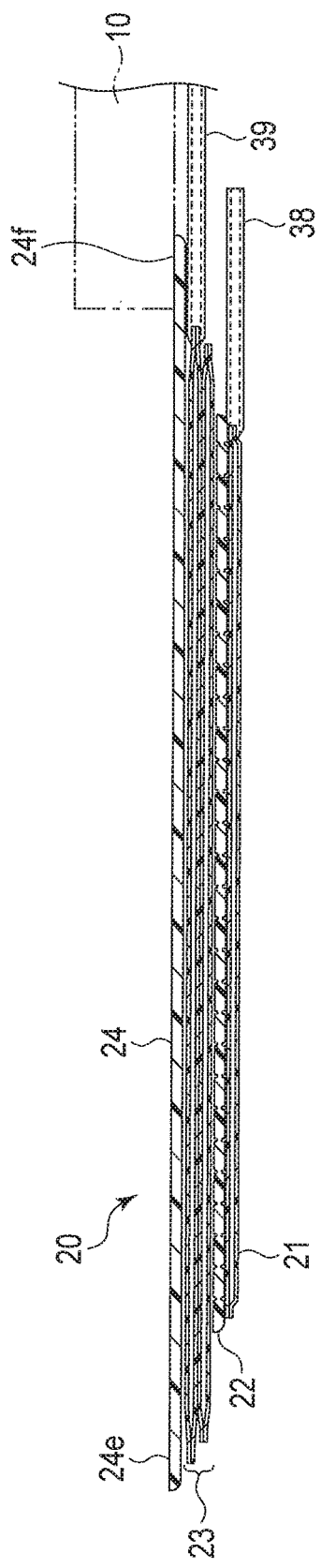
FIG. 3A is a cross-sectional view of the cuff structure of the blood pressure monitor illustrated in FIG. 2.
Figure 3B:
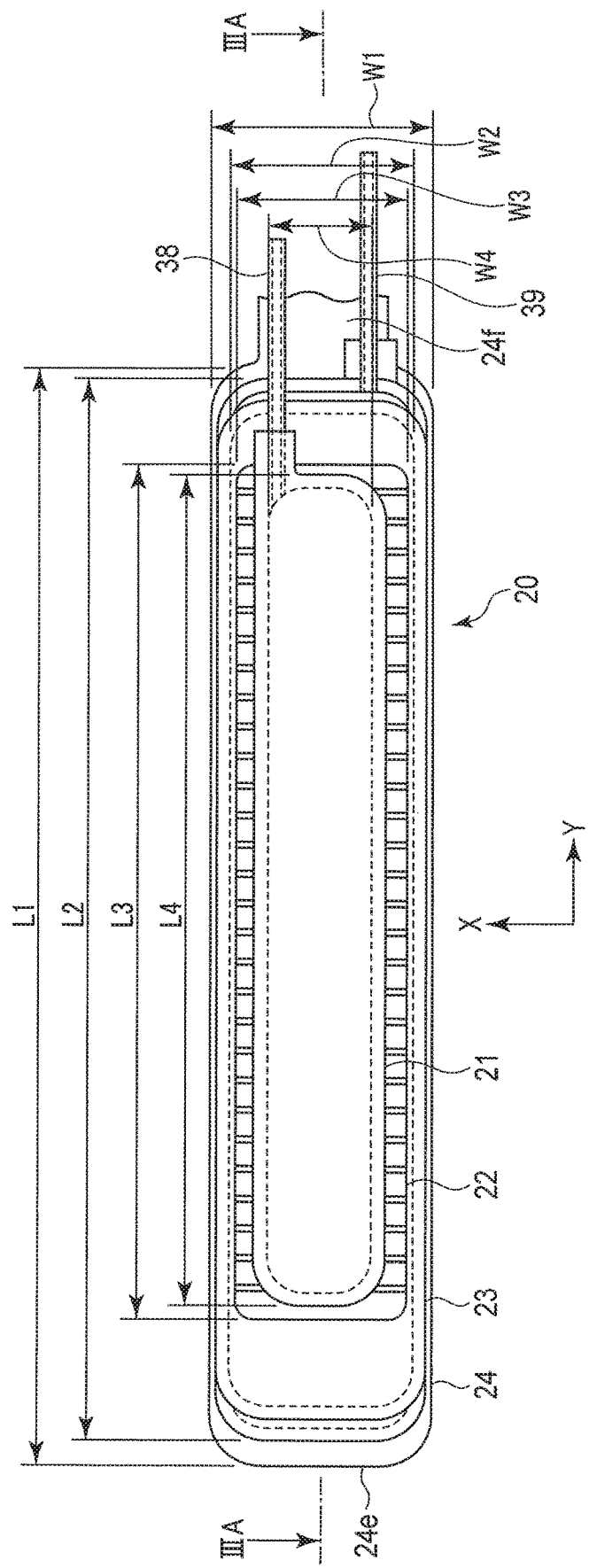
FIG. 3B is a plan view of the cuff structure illustrated in FIG. 3A, in a state of being developed to have an inner circumference surface serving as the forefront surface.

FIG. 3A is a cross-sectional view of the cuff structure of the blood pressure monitor illustrated in FIG. 2. FIG. 3B is a plan view of the cuff structure illustrated in FIG. 3A, in a state of being developed to have the inner circumference surface serving as the forefront surface. The cross-sectional view of FIG. 3A corresponds to a cross-sectional view taken along line IIIA-IIIA in FIG. 3B.

FIG. 4A is an enlarged cross-sectional view of a part of FIG. 3B. FIG. 4B is a cross-sectional view of the structure illustrated in FIG. 4A, taken along line IVB-IVB.

Figure 5A:
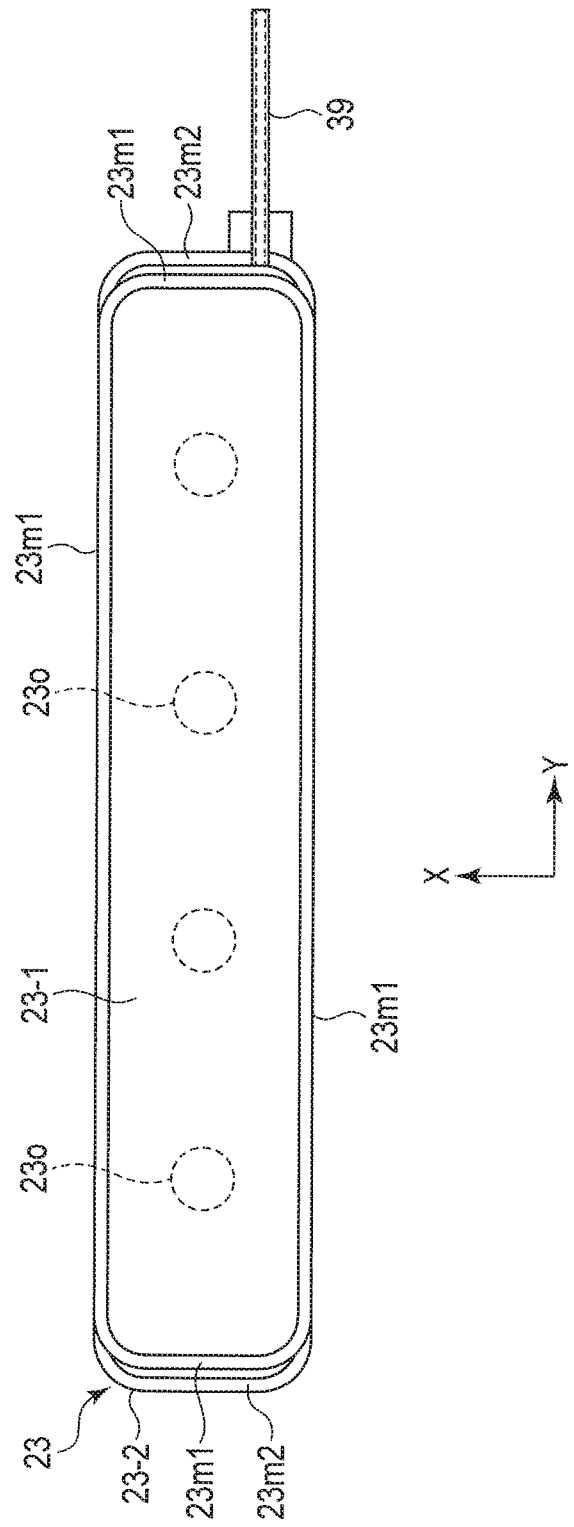
FIG. 5A is a plan view illustrating a pressure cuff of the cuff structure shown in FIGS. 3A and 3B.

FIG. 5A is a plan view illustrating a pressure cuff of the cuff structure illustrated in FIGS. 3A and 3B. FIG. 5B is a plan view of the back plate of the cuff structure illustrated in FIGS. 3A and 3B.

As illustrated in FIGS. 3A and 3B, each of the curler 24, the pressure cuff 23, the back plate 22, and the sensing cuff 21 has a strip shape elongated in one direction (Y direction). In this example, a length W1 of the curler 24 in the width direction X is 28 mm, a length W2 of the pressure cuff 23 in the width direction X is 25 mm (excluding welded edge portions on both sides), a length W3 of the back plate 22 in the width direction X is 23 mm, and a length W4 of the sensing cuff 21 in the width direction X is 15 mm (excluding welded edges on both sides). Furthermore, in this example, a length L1 of the curler 24 in the longitudinal direction Y is 148 mm (excluding the base portion 24f attached to the main body 10), a length L2 of the pressure cuff 23 in the longitudinal direction Y is 140 mm, a length L3 of the back plate 22 in the longitudinal direction Y is 114 mm, and a length L4 of the sensing cuff 21 in the longitudinal direction Y is 110 mm.

The sensing cuff 21 includes a first sheet 21A that comes into contact with the left wrist 90, and a second sheet 21B facing the first sheet 21A, as can be seen in FIGS. 4A and 4B. The second sheet 21B is disposed to face the inner circumference surface of the back plate 22, which is a part of the pressing member. The first sheet 21A and the second sheet 21B are formed to be a bag shape with their circumference edge portions 21m welded to each other. In this example, as illustrated in FIG. 4B, the sensing cuff 21 is provided with a slack 21r that extends in the longitudinal direction Y of the sensing cuff 21 in a natural state, at a location continuous with the edge portions 21m on both sides of the sensing cuff 21 in the width direction X. Furthermore, as illustrated in FIG. 4A, the first sheet 21A is provided with the slack 21r that extends in the width direction X of the sensing cuff 21 in a natural state at a location continuous with edge portions 21m on both sides of the sensing cuff 21 in the longitudinal direction Y (only the distal end side is illustrated in FIG. 4A). The slack 21r can be formed by a known method, for example, when welding or bonding the circumference edge portions 21m of the first sheet 21A and the second sheet 21B to each other. As can be seen in FIGS. 3A and 3B, an elastic tube 38 is attached to an end portion of the sensing cuff 21 on the base side (+Y side) in the longitudinal direction Y, for supplying a second fluid (air in this example) for pressure transmission to the sensing cuff 21 and for discharging the second fluid for pressure transmission from the sensing cuff 21. The first sheet 21A and the second sheet 21B are stretchable silicone resin sheets (thickness t=0.15 mm) in this example. The inner circumference surface 20a of the cuff structure 20 is formed by the first sheet 21A of the sensing cuff 21.

In the present specification, "comes into contact" not only includes direct contact but also includes indirect contact with another intervening member (for example, a cover member).

The pressure cuff 23 includes two fluid bags 23-1 and 23-2 stacked in the thickness direction, as can be seen in FIGS. 4A and 4B. Each of the fluid bags 23-1 and 23-2 is formed by welding circumference edge portions 23m1 and 23m2 of two stretchable thermoplastic polyurethane sheets (thickness t=0.15 mm) facing each other. As illustrated in FIG. 5A, the dimension in the longitudinal direction Y of the fluid bag 23-1, which is on the inner circumferential side, is set to be slightly smaller than the dimension (L2) in the longitudinal direction Y of the fluid bag 23-2, which is on the outer circumferential side. To the base side's (+Y side's) end portion in the longitudinal direction Y of the fluid bag 23-2, which is on the outer circumferential side, an elastic tube 39 is attached for supplying a first fluid (air in this example) for pressure transmission to the pressure cuff 23 or discharging the first fluid for pressure transmission from the pressure cuff 23. Furthermore, a plurality of (four in this example) through holes 23o are formed at positions between the fluid bag 23-1 on the inner circumferential side and the fluid bag 23-2 on the outer circumference side adjacent thereto. Thus, the first fluid for pressurization (air, in this example) can flow between the two fluid bags 23-1 and 23-2 through these through holes 23o. Thus, when the pressure cuff 23 receives the first fluid for pressurization supplied from the main body 10 through the elastic tube 39 in the mounted state, the two stacked fluid bags 23-1 and 23-2 are inflated to press the left wrist 90.

The back plate 22 is a plate that has a thickness of about 1 mm and is made of resin (polypropylene in this example) in this example. As can be seen in FIGS. 3A and 3B, the back plate 22 extends to be in a strip shape with a length overwhelming that of the sensing cuff 21 in the longitudinal direction Y (corresponding to the circumference direction of the left wrist 90). Thus, the back plate 22 functions as the reinforcing plate, and can transmit the pressing force from the pressure cuff 23 entirely over the longitudinal direction Y (corresponding to the circumference direction of the left wrist 90) of the sensing cuff 21. Furthermore, as can be seen in FIGS. 4A and 5B, an inner circumference surface 22a and an outer circumference surface 22b of the back plate 22 are respectively provided with a plurality of grooves 22d1 and 22d2 that have U or V cross-sectional shape, extending in the width direction X, and are provided to be in parallel while being spaced apart from each other in the longitudinal direction Y. In this example, the grooves 22d1 on the inner circumference surface 22a of the back plate 22 and the grooves 22d2 on the outer circumference surface 22b of the back plate 22 are provided at the same positions in the longitudinal direction Y. Thus, the back plate 22 is thinner and thus can be more easily bent at the positions of the grooves 22d1 and 22d2 compared with other positions. Therefore, the back plate 22 does not hinder the curving of the cuff structure 20 along the circumference direction Y of the left wrist 90, at the time of mounting on the subject with the belt 2 collectively wound around the left wrist 90 and the cuff structure 20.

Figure 7:
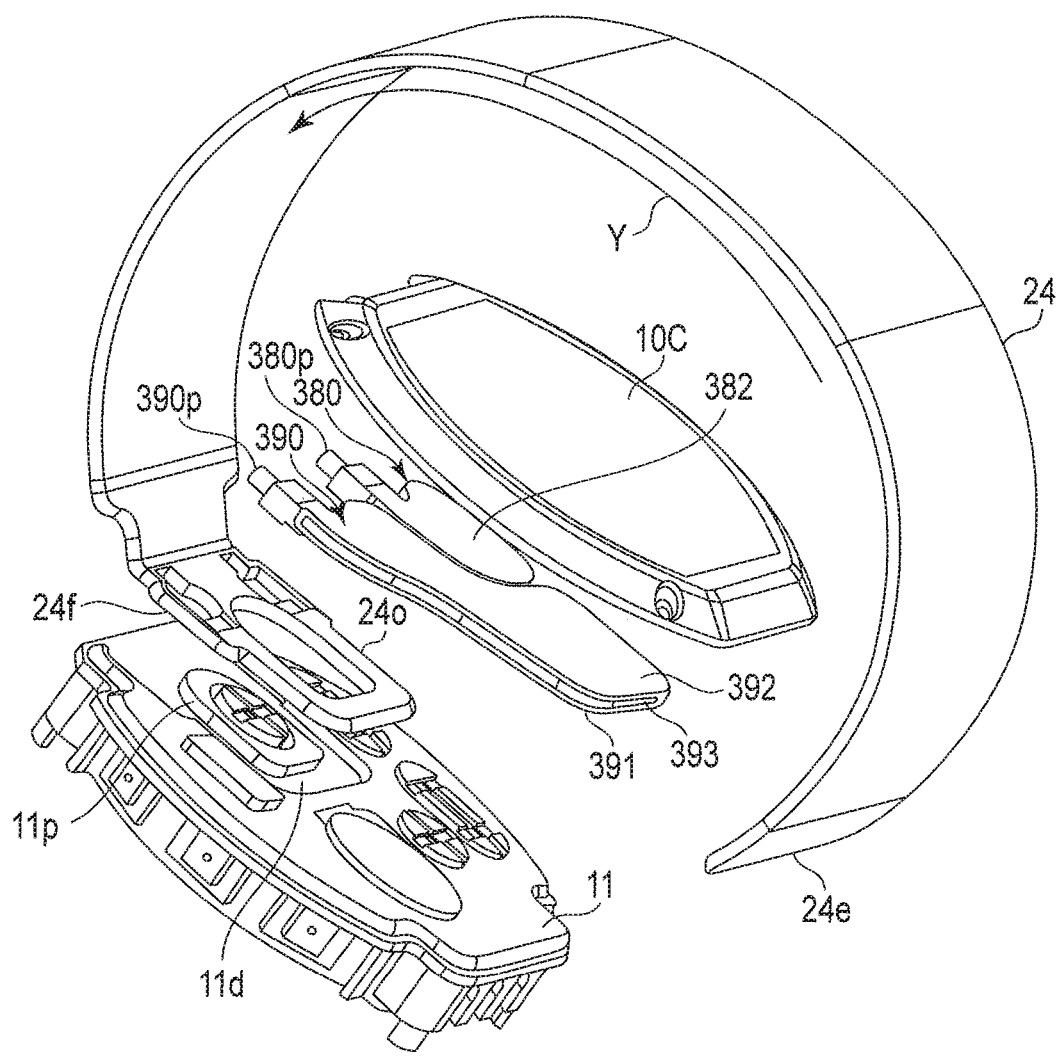
FIG. 7 is an exploded perspective view illustrating the main body illustrated in FIG. 6 and the curler of the blood pressure monitor illustrated in FIGS. 1 and 2.

The curler 24 in this example is a resin plate (in this example, a polypropylene plate) having a thickness of about 1 mm and having a certain degree of flexibility and hardness. As can be seen in FIGS. 3A and 3B, the curler 24 in a developed state extends to be in a strip shape with a length overwhelming that of the pressure cuff 23 in the longitudinal direction Y (corresponding to the circumference direction of the left wrist 90). The curler 24 in a natural state has a curved shape along the circumference direction Y around the left wrist 90, as illustrated in FIG. 7. Thus, the shape of the cuff structure 20 in the natural state is maintained to be in the curved state along the circumference direction Y of the left wrist 90 as illustrated in FIG. 2.

The circumference edge portion of the inner circumference surface 22a of the back plate 22 and the circumference edge portion of the inner circumference surface 24a of the curler 24 respectively have rounded portions 22r and 24r curved in a direction away from the measurement site (in this example, the left wrist 90). Thus, the subject does not feel discomfort when mounting the cuff structure 20.

Figure 6:
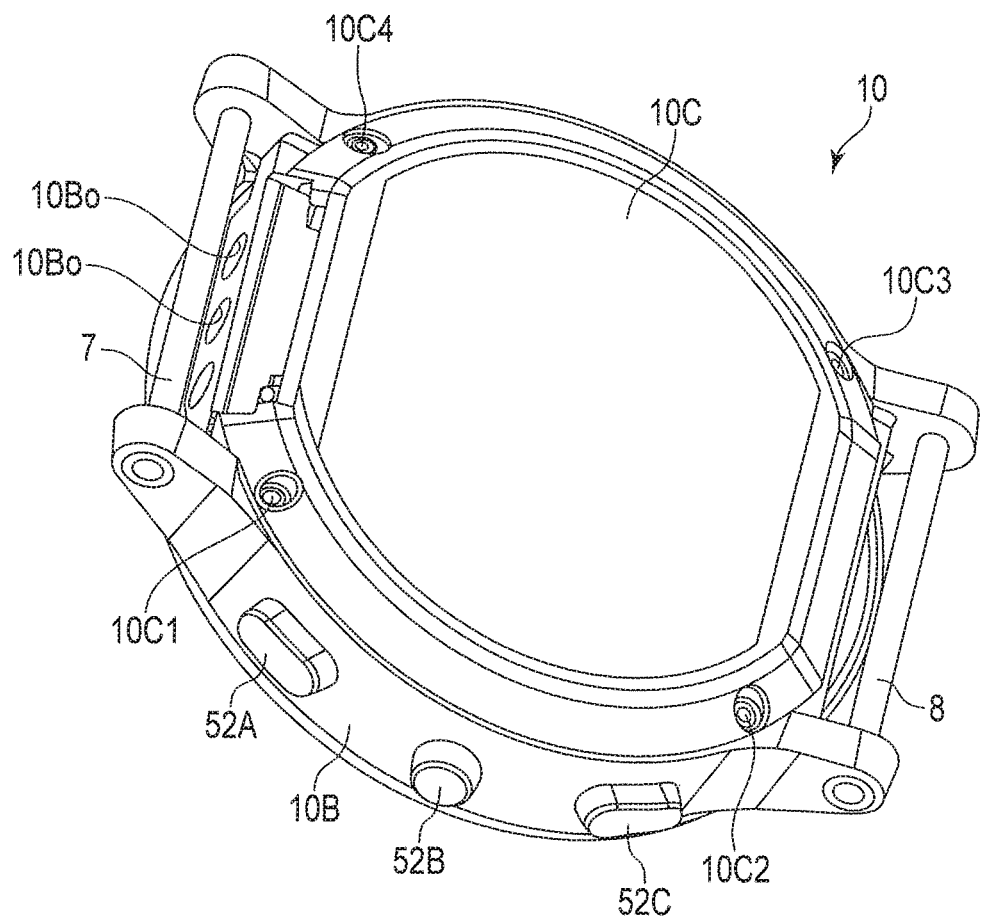
FIG. 6 is a perspective view illustrating the back side of the main body of the blood pressure monitor illustrated in FIGS. 1 and 2.

FIG. 6 is a perspective view illustrating the back side of the main body of the blood pressure monitor illustrated in FIGS. 1 and 2.

As illustrated in FIG. 6, a back cover 10C is provided on the back side of the main body 10. The back cover 10C has four through-holes, and is fixed to the back side of the case 10B by means of screws 10C1, 10C2, 10C3 and 10C4 at the positions of these through-holes. Filter-equipped intake/exhaust holes 10Bo are provided in a portion of the side surface of the case 10B which is hidden by the base portion 3e of the first belt portion 3 (the same applies to the portion hidden by the base portion 4e of the second belt portion 4). Thus, air can flow between the inside and the outside of the case 10B while achieving a water resistant function.

FIG. 7 is an exploded perspective view illustrating the main body illustrated in FIG. 6 and the curler of the blood pressure monitor illustrated in FIGS. 1 and 2.

As illustrated in FIG. 7, the case 10B of the main body 10 accommodates an inner case member 11 for installing the blood pressure measurement elements. On the back side of the inner case member 11, an annular groove 11d surrounding an area around a protrusion 11p is formed. A ring 24o having a shape corresponding to the annular groove 11d is formed at the base portion 24f of the curler 24. When assembling the main body 10, the ring 24o of the base portion 24f of the curler 24 is fitted in the annular groove 11d of the inner case member 11 (at the same time, the ring 24o is fitted on the protrusion 11p of the inner case member 11).

The base portion 24f of the curler 24 is sandwiched between the back side of the inner case member 11 and the back cover 10C of the main body 10, while overlapping with two flow path-forming members (a first flow path-forming member 390 and a second flow path-forming member 380) described later.

Thus, as illustrated in FIG. 2, one end 20f of the cuff structure 20 (the base portion 24f of the curler 24) is attached to the main body 10. The other end 20e (the distal end portion 24e of the curler 24) of the cuff structure 20 is a free end. As a result, the cuff structure 20 faces the inner circumference surfaces 3a and 4a of the belt 2, while being separable from the inner circumference surfaces 3a and 4a.

When the cuff structure 20 is attached to the main body 10 in this manner, the one end 20f of the cuff structure 20 is reliably held by the main body 10. Furthermore, at the time of maintenance service, the cuff structure 20 can be exchanged for the main body 10 regardless of the belt 2, with the back cover 10C of the main body 10 open. The length of the cuff structure 20 in the longitudinal direction Y (corresponding to the circumference direction of the left wrist 90) can be set to an optimum length independently from the belt 2.

In this blood pressure monitor 1, the main body 10 and the belt 2 are formed separately from each other, and the belt 2 is attached to the main body 10. Therefore, during maintenance service, the belt 2 on the main body 10 can also be exchanged independently from the cuff structure 20.

Figure 9:
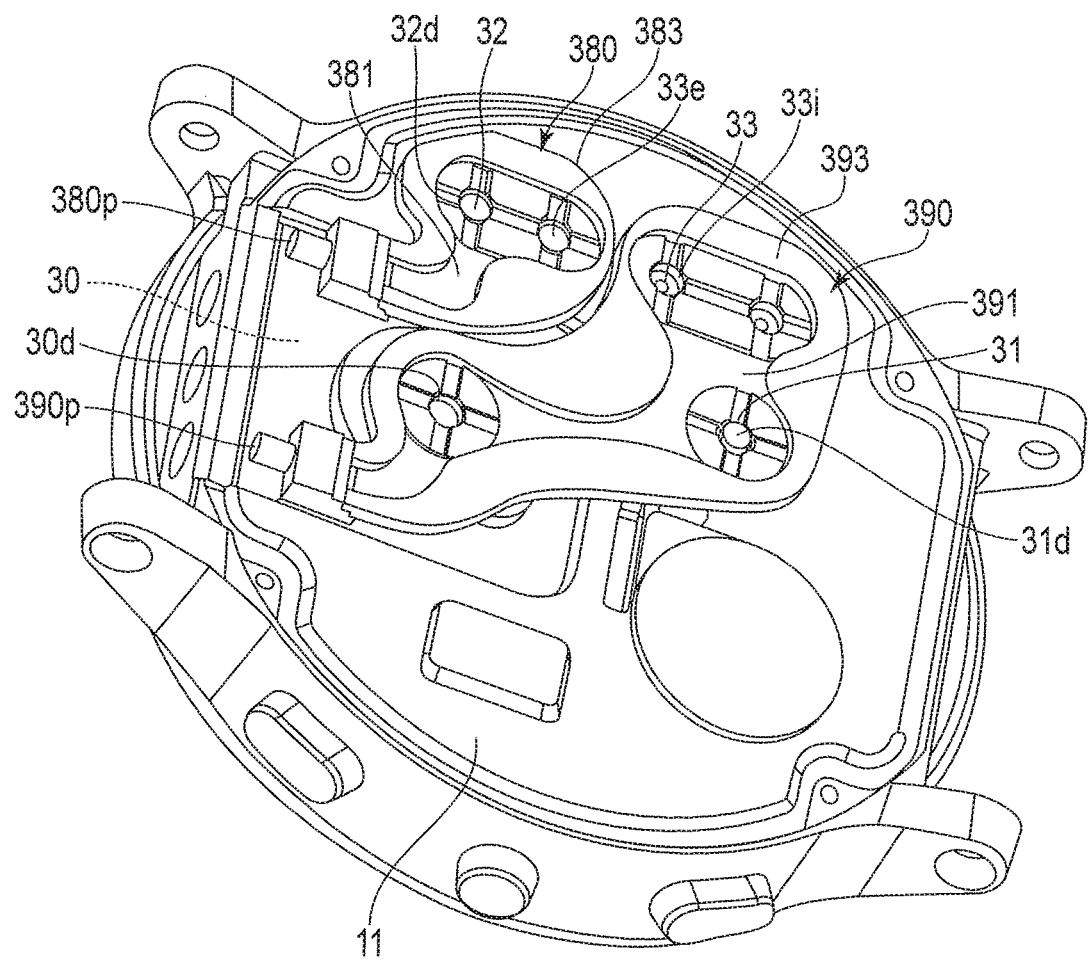
FIG. 9 is a perspective view depicting another part of the internal structure of the main body illustrated in FIG. 6.

The first flow path-forming member 390 illustrated in FIG. 7 includes two sheet plates 391 and 392 facing each other and extending to be in a thin plate shape, and a spacer portion 393 keeping a predetermined distance (0.7 mm in this example) between the sheet plates 391 and 392. Similarly, the second flow path-forming member 380 includes two sheet plates 381 and 382 facing each other and extending to be in a thin plate shape, and a spacer portion 383 keeping a predetermined distance between the sheet plates 381 and 382. The sheet plate 381 and the spacer portion 383 are illustrated in FIG. 9 to be described later (in FIG. 9, illustration of the sheet plates 392 and 382 far from the inner case member 11 is omitted for easier understanding). Lateral pins 390p and 380p are attached to an end portion of the first flow path-forming member 390 and an end portion of the second flow path-forming member 380, respectively, so as to allow fluid flow. When the cuff structure 20 including the curler 24 is attached to the main body 10, the elastic tube 39 from the pressure cuff 23 is connected to the first flow path-forming member 390 via the lateral pin 390p. At the same time, the elastic tube 38 from the sensing cuff 21 is connected to the second flow path-forming member 380 via the lateral pin 380p.

The first flow path-forming member 390 and the second flow path-forming member 380 are formed by integrally molding elastomer in this example. The thicknesses of the first flow path-forming member 390 and the second flow path-forming member 380 are each set to 1.2 mm in this example.

Figure 10:
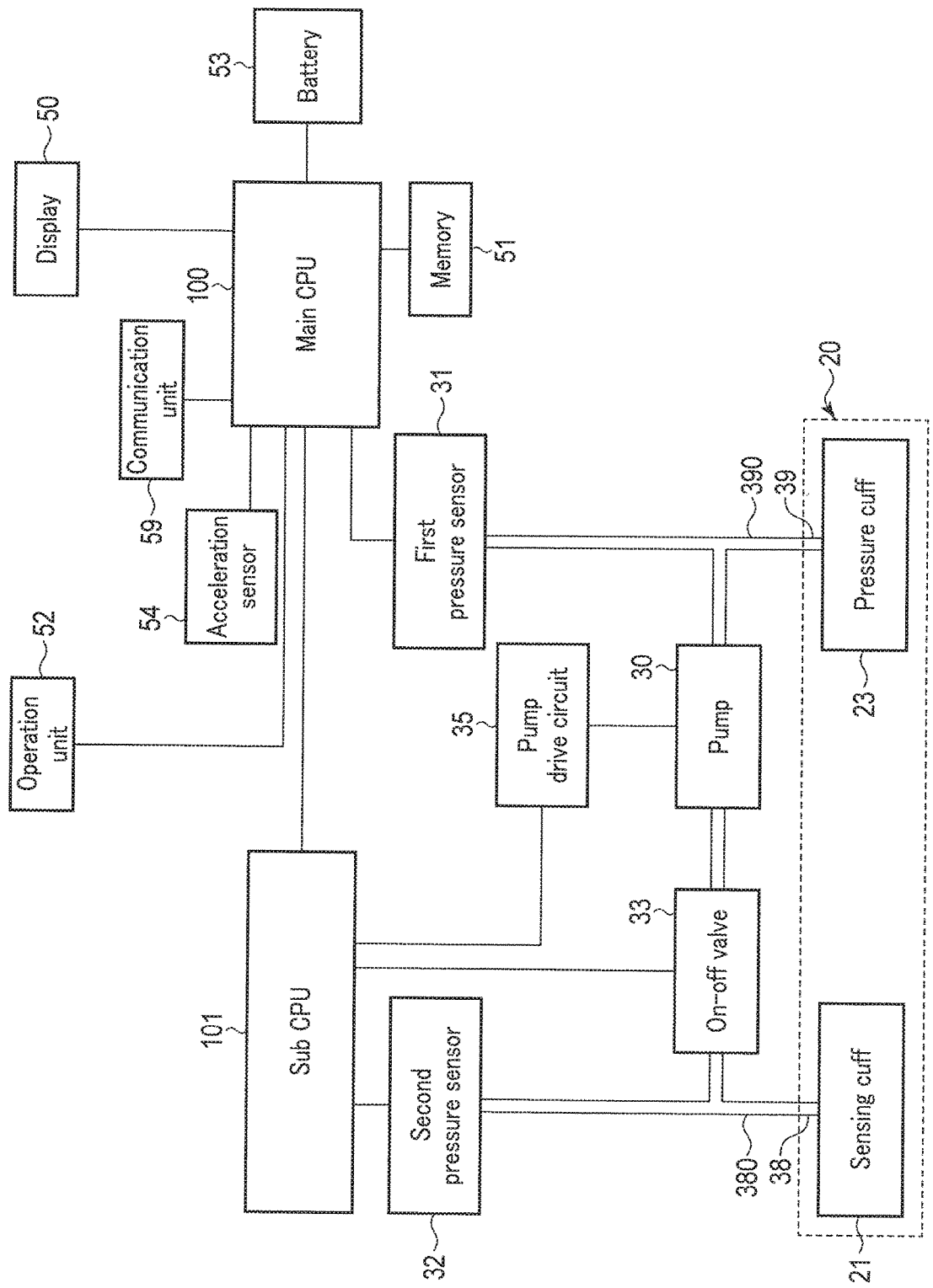
FIG. 10 is a block diagram of the blood pressure monitor shown in FIGS. 1 and 2.

FIG. 10 is a block diagram of the blood pressure monitor illustrated in FIGS. 1 and 2.

The main body 10 of the blood pressure monitor 1 includes, in addition to the display 50 and the operation unit (input unit) 52 including the switches 52A to 52C described above, the blood pressure measurement elements for performing blood pressure measurement including: a main central processing unit (CPU) 100 and sub CPU 101 serving as a controller; a memory 51 serving as storage unit; an acceleration sensor 54; a communication unit 59; a battery 53; a first pressure sensor 31 for detecting pressure of the pressure cuff 23; a second pressure sensor 32 for detecting pressure of the sensing cuff 21; a pump 30; an on-off valve 33; and a pump drive circuit 35 for driving the pump 30. The main CPU 100 mainly controls the operation of the entire blood pressure monitor 1, and sub CPU 101 mainly controls the operation of an air system. Hereinafter, for the sake of simplicity, the main CPU 100 and the sub CPU 101 will be collectively and simply referred to as a CPU 100.

The operation unit 52 includes the switches 52A to 52C described with reference to FIGS. 1 and 2. The switch 52A is used to input an instruction to start or stop blood pressure measurement in the blood pressure measurement mode, and is used to select a setting item in the setting mode. The switch 52B is used to switch between the setting mode, the blood pressure measurement mode, and the like, and is also used to input an instruction for determining the selected selection item in the setting mode. The switch 52C is used to input an instruction to cancel the determination in the setting mode, and is used to input an instruction to cause the display 50 to display a measurement record of blood pressure, activity amount, and the like in the past in the blood pressure measurement mode.

The switches 52A to 52C form the operation unit, which is an example of the input unit as described above. The operation unit is not limited to the push-type switch, and may be, for example, another touch-type input apparatus such as a pressure-sensitive (resistive) or proximity-type (electrostatic capacitive) touch panel. Alternatively, the input unit may be an audio-based input apparatus provided with a microphone, or a communication-based input apparatus that enables wired or wireless communication with a computer, a smartphone, or the like. Alternatively, the input unit may be a combination of two or more of the contact-based input apparatus, the audio-based input apparatus, and the communication-based input apparatus.

The input unit is used by the subject to input information which is biometric information including, for example, blood pressure measured by an upper arm blood pressure monitor, a circumference length of a measurement site (a wrist in this example), body fat percentage, and the like. Further, the input unit is used for input of an instruction by a subject, for example, an instruction for starting blood pressure measurement or an instruction for stopping blood pressure measurement. The input unit outputs the input information or instruction to the CPU 100.

The memory 51 non-temporarily stores data about a program for controlling the blood pressure monitor 1, data used to control the blood pressure monitor 1, setting data for setting various functions of the blood pressure monitor 1, data about measurement results of blood pressure values, and the like. The memory 51 is also used as a work memory for executing a program and the like.

Here, the setting data for setting various functions of the blood pressure monitor 1 includes biometric information input by the subject by using the operation unit 52. Furthermore, the data used to control the blood pressure monitor 1 includes data corresponding to a relational expression or table used to calculate the amount (target supply amount) of the second fluid to be supplied to the sensing cuff 21 from the above biometric information.

The CPU 100 executes various functions to serve as the controller in accordance with a program for controlling the blood pressure monitor 1 stored in the memory 51. For example, the CPU calculates the amount (target supply amount) of the second fluid to be supplied to the sensing cuff 21 based on the biometric information input by the subject by using the operation unit 52 and the above-described relational expression or table. When the blood pressure measurement function is executed, upon receiving an instruction to start blood pressure measurement input via the switch 52A of the operation unit 52, the CPU 100 performs control to drive the pump 30 and the on-off valve 33 based on signals from the first pressure sensor 31 and the second pressure sensor 32. Then, the CPU100 performs control to calculate a blood pressure value, pulse, and the like based on the signal from the second pressure sensor 32.

The acceleration sensor 54 includes a three-axis acceleration sensor built in the main body 10. The acceleration sensor 54 outputs an acceleration signal, representing acceleration in three directions orthogonal to each other, to the CPU 100. In this example, the output of the acceleration sensor 54 is used to measure the activity amount.

The communication unit 59 transmits predetermined information to an external apparatus through a network or receives information from an external apparatus through the network, and transfers the information to the CPU 100, under the control performed by the CPU 100. Communications performed through this network may be any of wireless communications and wired communications. In this embodiment, the network is the Internet, but is not limited thereto, and may be another type of network such as a hospital Local Area Network (LAN), or one-to-one communications using a USB cable may be employed. The communication unit 59 may include a micro USB connector.

The battery 53 is a rechargeable secondary battery in this example. The battery 53 supplies power to the elements installed in the main body 10, which are, in this example, the CPU 100, the memory 51, the acceleration sensor 54, the communication unit 59, the first pressure sensor 31, the second pressure sensor 32, the pump 30, the on-off valve 33, and the pump drive circuit 35.

The pump 30 is a part of an adjuster that adjusts the amount of the first fluid in the pressure cuff 23 and the amount of second fluid in the sensing cuff. The pump 30 is a piezoelectric pump in this example, and is driven by the pump drive circuit 35 based on a control signal supplied from the CPU 100. The pump 30 is in fluid connection with the pressure cuff 23 via the first flow path-forming member 390 and the elastic tube 39 that form the first flow path. The pump 30 can supply air, serving as the first fluid for pressurization, to the pressure cuff 23 through the first flow path-forming member 390 and the elastic tube 39. The pump 30 is equipped with an exhaust valve (not illustrated) whose opening and closing are controlled in accordance with the on/off of the pump 30. Specifically, the exhaust valve is closed when the pump 30 is turned ON to assist entrapping of the air in the pressure cuff 23, and is opened when the pump 30 is turned OFF to cause the air in the pressure cuff 23 to be discharged to the atmosphere through the elastic tube 39 and the first flow path-forming member 390. This exhaust valve has the function of a check valve, so that the discharged air does not flow back.

The pump 30 is in fluid connection with the sensing cuff 21 via the second flow path-forming member 380 and the elastic tube 38 that form the second flow path. The on-off valve (in this example, a normally open solenoid valve) 33 is interposed in the second flow path (actually, between the first flow path-forming member 390 and the second flow path-forming member 380). The on-off valve 33 and the pump 30 form the above-described adjuster.

Opening/closing (opening degree) of the on-off valve 33 is controlled based on a control signal from the CPU 100. When the on-off valve 33 is in the open state, air serving as the second fluid for pressure transmission from the pump 30 can be supplied to and stored in the sensing cuff 21 through the second flow path.

In this example, each of the first pressure sensor 31 and the second pressure sensor 32 is a piezoresistive pressure sensor. The first pressure sensor 31 detects the pressure in the pressure cuff 23 via the first flow path-forming member 390 and the elastic tube 39 that form the first flow path. The second pressure sensor 32 detects the pressure in the sensing cuff 21 via the second flow path-forming member 380 and the elastic tube 38 that form the second flow path.

Figure 8:
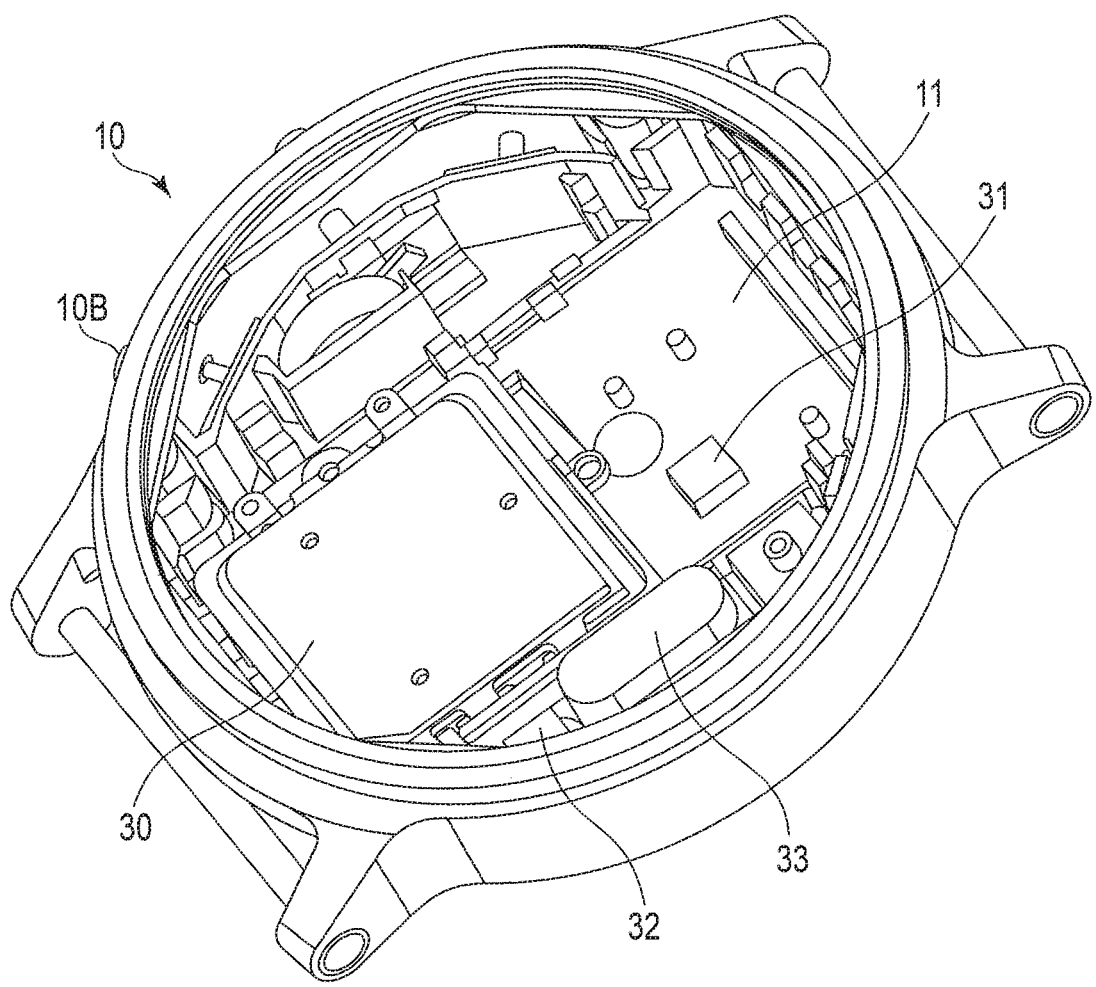
FIG. 8 is a perspective view depicting a part of the internal structure of the main body illustrated in FIG. 6.

As illustrated in FIG. 8 (illustrating the main body 10 as viewed obliquely from above), the pump 30 and the first pressure sensor 31 are disposed substantially at the center of the inner case member 11 in the main body 10. The on-off valve 33 and the second pressure sensor 32 are disposed around the inner case member 11. As illustrated in FIG. 9 (illustrating the inside of the main body 10 as viewed obliquely from below), the first flow path-forming member 390 is provided on the back side of the inner case member 11, and is provided over a discharge port 30d of the pump 30, an air inlet 31d of the first pressure sensor 31, and an inlet 33i of the on-off valve 33. The second flow path-forming member 380 is provided on the back side of the inner case member 11, and is provided over an outlet 33e of the on-off valve 33 and an air inlet 32d of the second pressure sensor 32.

With the above-described blood pressure measurement elements installed in the main body 10, the blood pressure monitor 1 has a compact and integrated configuration. Thus, excellent usability is offered to the subject.

Blood Pressure Measurement Method

Figure 11:
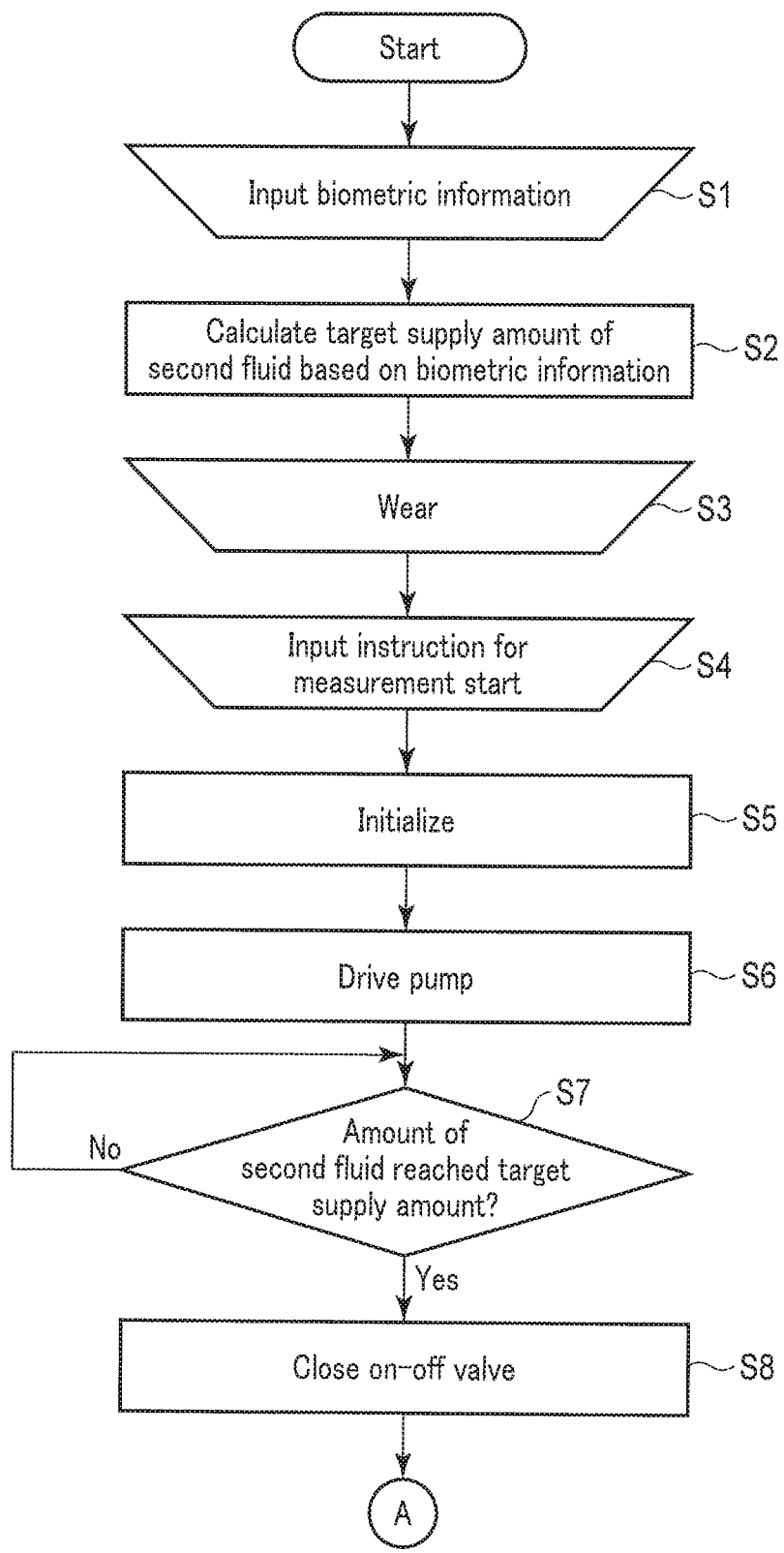
FIG. 11 is a flowchart illustrating some steps of a blood pressure measurement method according to one example.

FIG. 11 is a flowchart illustrating some steps of a blood pressure measurement method according to one example. FIG. 12 is a flowchart showing the remaining steps of the blood pressure measurement method the some steps of which are illustrated in FIG. 11.

In this method, first of all, the subject inputs biometric information to the blood pressure monitor 1, as illustrated in step S1 in FIG. 11. The biometric information is input by operating the switches 52A to 52C of the operation unit 52.

The biometric information is information that may affect the blood pressure measurement accuracy, such as the blood pressure of the subject, the position of the artery and bone at the measurement site, the amount of fat, and the circumference length of the measurement site. The biometric information preferably includes at least one of the blood pressure of the subject and the circumference length of the measurement site. Moreover, when using the blood pressure value of the subject as at least a part of the biometric information, this blood pressure is preferably measured by an upper arm type blood pressure monitor. Here, as an example, the biometric information is assumed to be the blood pressure measured by the upper arm type blood pressure monitor.

When the biometric information is input to the blood pressure monitor 1, the CPU 100 calculates the amount of the second fluid to be supplied to the sensing cuff 21, that is, the target supply amount, based on the biometric information as illustrated in step S2 in FIG. 11. Specifically, the target supply amount is calculated from this biometric information and the above-mentioned relational expression or table stored in the memory 51. The memory 51 stores this target supply amount.

Next, the subject mounts the blood pressure monitor 1 on his or her measurement site, which is the left wrist in this example, as illustrated in step S3 of FIG. 11.

Figure 13A:
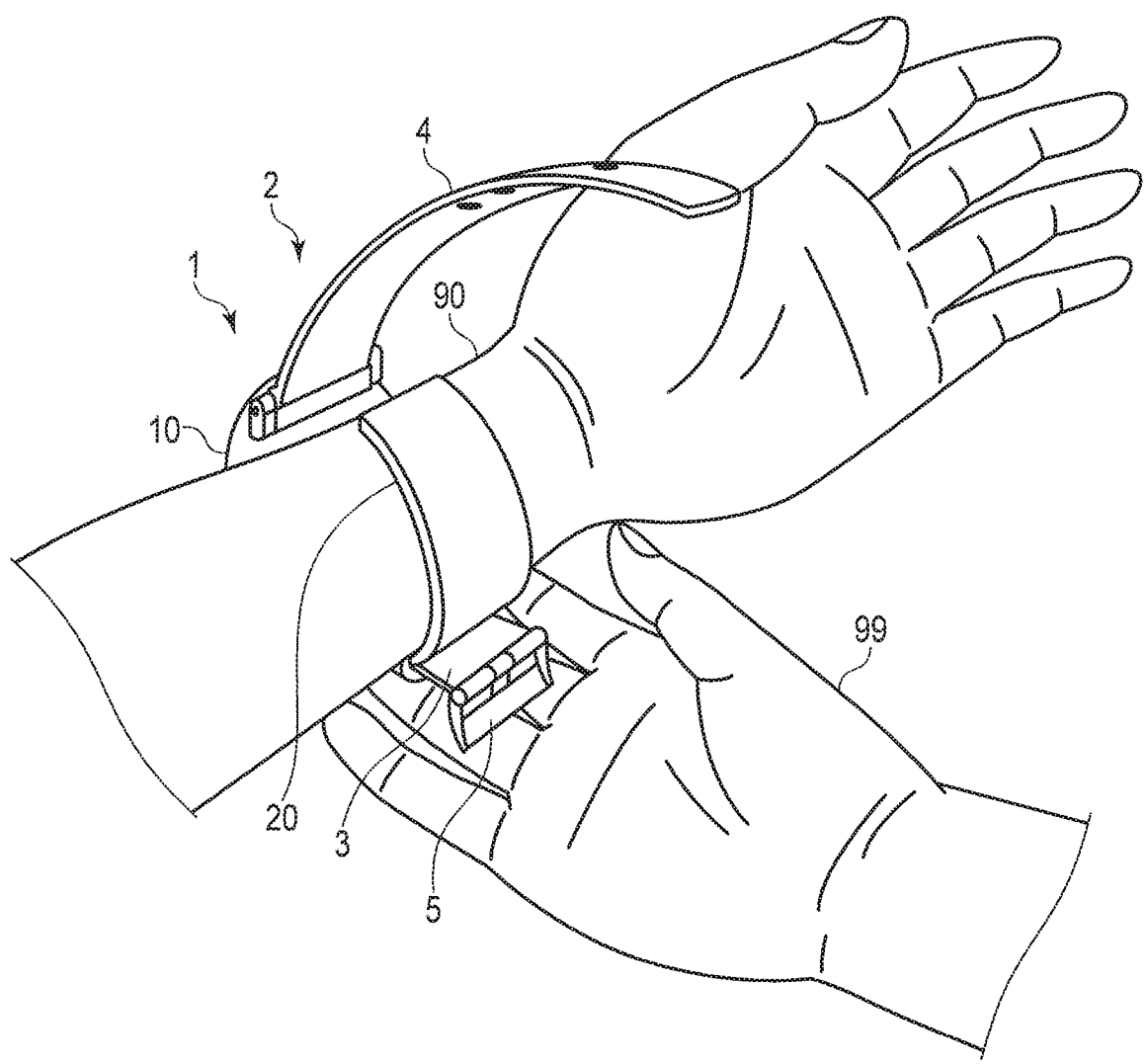
FIG. 13A is a perspective view illustrating how a subject winds the blood pressure monitor illustrated in FIGS. 1 and 2 on the left wrist.

Specifically, first of all, the subject puts the cuff structure 20 on the left wrist 90 using his or her right hand 99 as illustrated in FIG. 13A. Here, the cuff structure 20 in the natural state is curved along the circumference direction Y of the left wrist 90 due to the curler 24. Therefore, the subject can easily put the cuff structure 20 on the left wrist 90 by placing the inner circumference surface of the cuff structure 20 to the outer circumference surface of the left wrist 90 using the right hand 99 in this example. In a state where the cuff structure 20 is mounted on the left wrist 90, the cuff structure 20 holds the left wrist 90 even after the subject has released the right hand 99 from the cuff structure 20. Thus, the cuff structure 20 (as well as the belt 2 and the main body 10) is less likely to come off the left wrist 90.

Next, as illustrated in FIG. 13B, the subject uses the right hand 99 to wind the belt 2 and the cuff structure 20 collectively around the left wrist 90. Specifically, the portion continuous with the distal end portion 4f of the second belt portion 4 is passed through the frame 5A of the buckle 5 of the first belt portion 3 and the tongue 5B of the buckle 5 is inserted in any one of the plurality of small holes 4w of the second belt portion 4. In this manner, the first belt portion 3 and the second belt portion 4 are fastened as illustrated in FIG. 13C. Thus, the belt 2 extending from the main body 10 is wound around the left wrist 90, and the strip-shaped cuff structure 20 having the one end 20f attached to the main body 10 is disposed on the inner circumference side that is closer to the left wrist 90 than the belt 2 is.

In this state, in the blood pressure monitor 1, the cuff structure 20 can be separated from the inner circumference surfaces 3a and 4a of the belt 2, and the other end 20e opposite to the one end 20f of the cuff structure 20 is a free end. Thus, when the first belt portion 3 and the second belt portion 4 are fastened, the cuff structure 20 receives inward force from the belt 2 so that the cuff structure 20 can slide or deform to conform well to the outer circumference surface of the left wrist 90. As a result, in the mounted state, the cuff structure 20 and the belt 2 are in close contact with the outer circumference surface of the left wrist 90 in this order, and thus are wound around the left wrist 90 while being in a strip shape as a whole. Thus, the blood pressure monitor 1 can be easily mounted on the left wrist 90.

Figure 14:
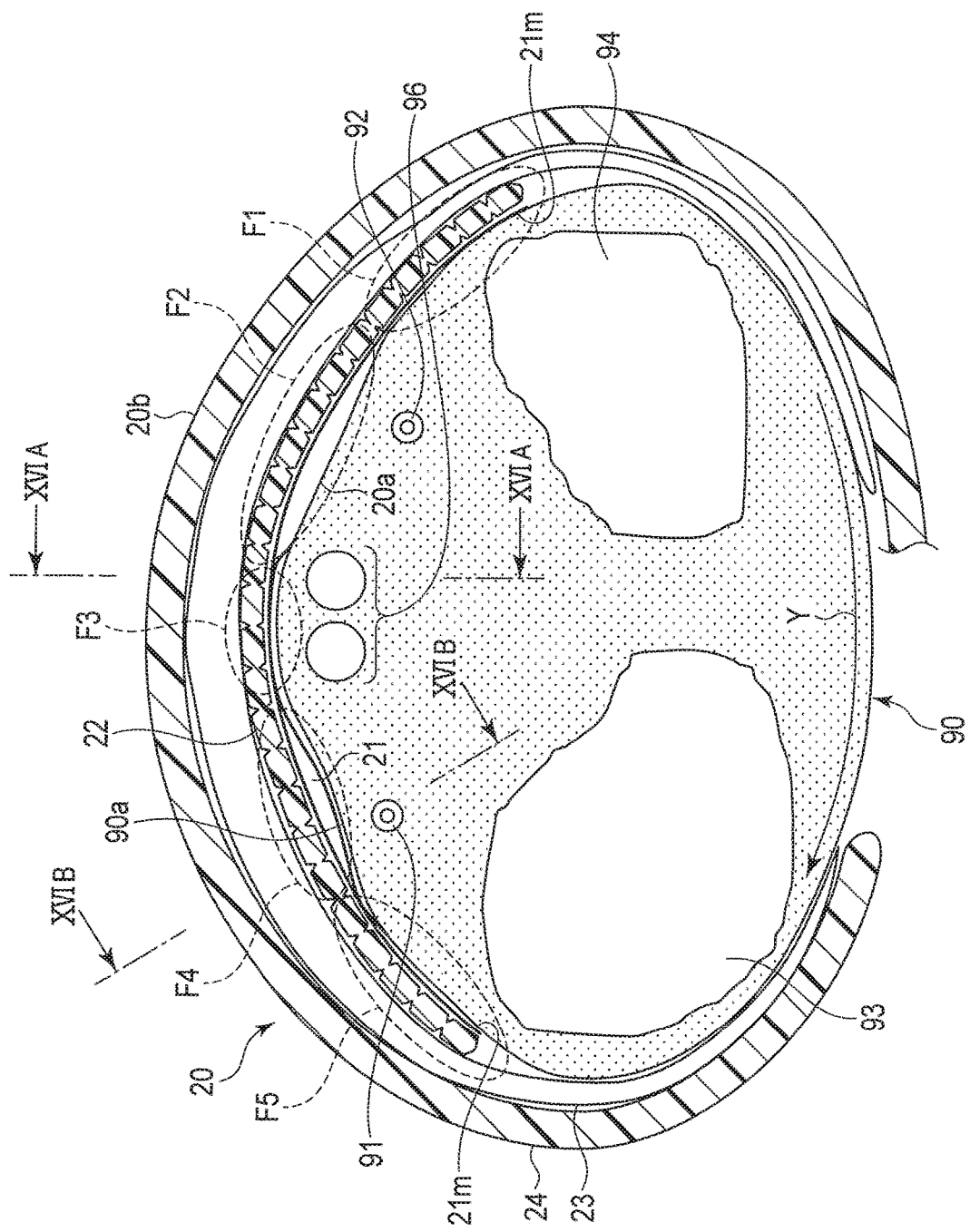
FIG. 14 is a cross-sectional view schematically illustrating a state where the blood pressure monitor illustrated in FIGS. 1 and 2 is mounted on the left wrist of the subject.

Specifically, as illustrated in FIG. 14, in this mounted state, a bag-like pressure cuff 23 extends along the circumference direction Y of the left wrist 90 on the inner circumference side of the curler 24 of the cuff structure 20. In addition, the bag-like sensing cuff 21 of the cuff structure 20 is disposed on the inner circumference side of the pressure cuff 23 to be in contact with the left wrist 90 and extends in the circumference direction Y across an artery-passing portion 90a of the left wrist 90. Furthermore, the back plate 22 of the cuff structure 20 is interposed between the pressure cuff 23 and the sensing cuff 21 and extends along the circumference direction Y of the left wrist 90. Note that the main body 10 and the belt 2 are omitted in FIG. 14. FIG. 14 illustrates a radius 93, an ulna 94, a radial artery 91, an ulnar artery 92, and a tendon 96 of the left wrist 90.

In this state, as in step S4 of FIG. 11, when the subject inputs a measurement start instruction via the switch 52A, the blood pressure monitor 1 performs initialization as in step S5 of FIG. 11. Specifically, the CPU 100 initializes a processing memory area. Furthermore, the CPU 100 turns OFF the pump 30 using the pump drive circuit 35, opens an exhaust valve built in the pump 30, and maintains the on-off valve 33 in the open state, so that air in the pressure cuff 23 and the sensing cuff 21 is discharged. Then, the first pressure sensor 31 and the second pressure sensor 32 are controlled to be adjusted to 0 mmHg.

Next, the CPU 100 drives the pump 30 using the pump drive circuit 35 while keeping the on-off valve 33 open (step S6 in FIG. 11). Thereby, pressurization of the pressure cuff 23 and the sensing cuff 21 starts. In this pressurization process, the pump 30 is driven using the pump drive circuit 35 while the first pressure sensor 31 and the second pressure sensor 32 monitor the pressure of the pressure cuff 23 and the sensing cuff 21. As a result, the first and the second fluid, which are air, are sent to the pressure cuff 23 and the sensing cuff 21 through the first flow path (the first flow path-forming member 390 and the elastic tube 39) and the second flow path (the second flow path-forming member 380 and the elastic tube 38), respectively.

Next, as in step S7 of FIG. 11, the CPU 100 determines whether the amount of the second fluid supplied to the sensing cuff 21 has reached the target supply amount. For example, the CPU 100 determines, based on the output from the first pressure sensor 31 or the second pressure sensor 32, whether the pressure of the sensing cuff 21 has reached the pressure (for example, 15 mmHg) corresponding to the target supply amount. Alternatively, the CPU 100 determines whether a driving time of the pump 30 has a reached a time with which the target supply amount is achieved (for example, 3 seconds). When the result of the determination in step S7 is NO, the CPU 100 makes the above determination again while keeping the on-off valve 33 open and the pump 30 driven. When the result of the determination in step S7 is YES, the CPU 100 controls the operation of the on-off valve 33 to close the on-off valve 33 while keeping the pump 30 driven (step S8 in FIG. 11).

Figure 17:
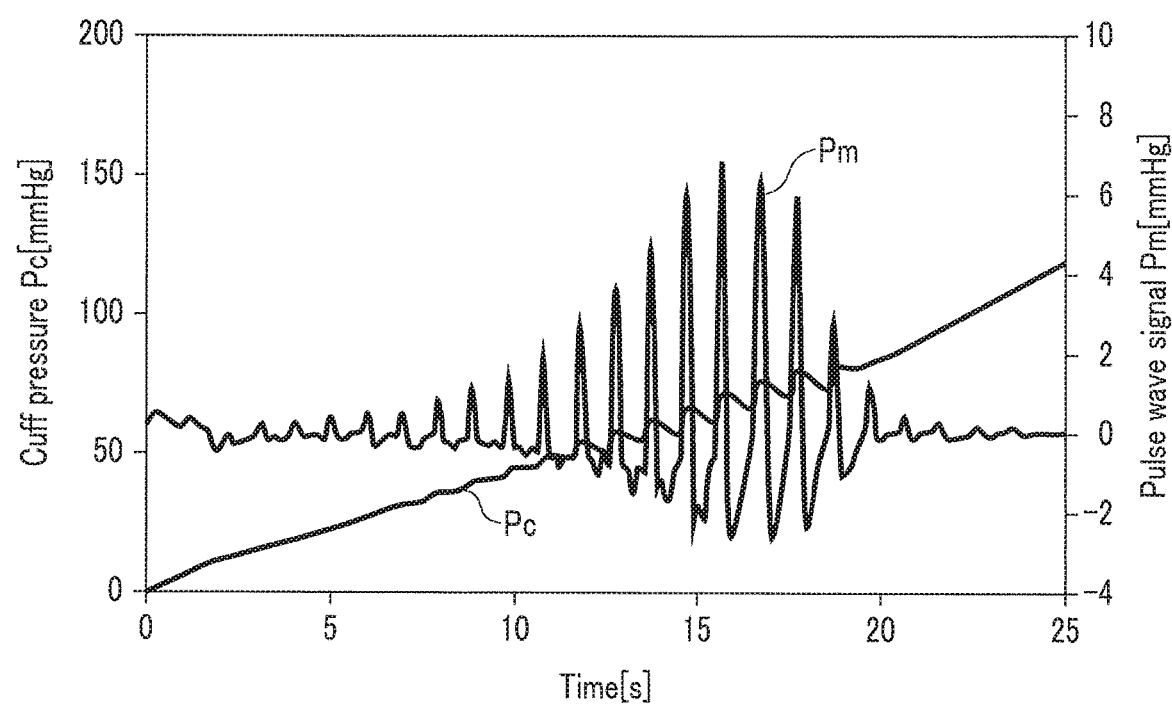
FIG. 17 is a graph showing an example of pressure Pc of the sensing cuff and a pulse wave signal Pm detected by the second pressure sensor included in the main body illustrated in FIGS. 8 and 9.

When the on-off valve 33 is closed while the pump 30 is kept driven, the pressure in the pressure cuff 23 gradually rises while the amount of the second fluid in the sensing cuff 21 is kept constant. The pressing force generated due to this pressure rise is transmitted to the sensing cuff 21 through the back plate 22. Thus, the sensing cuff 21 compresses the left wrist 90 (including the artery-passing portion 90a). During this pressurization process, the CPU 100 monitors pressure Pc of the sensing cuff 21, that is, the pressure of the artery-passing portion 90a of the left wrist 90 using the second pressure sensor 32 in order to calculate the blood pressure value, and acquires a pulse wave signal Pm serving as a variable component. FIG. 17 illustrates waveforms of the pressure Pc of the sensing cuff 21 and the pulse wave signal Pm obtained in this pressurization process.

Figure 16A:
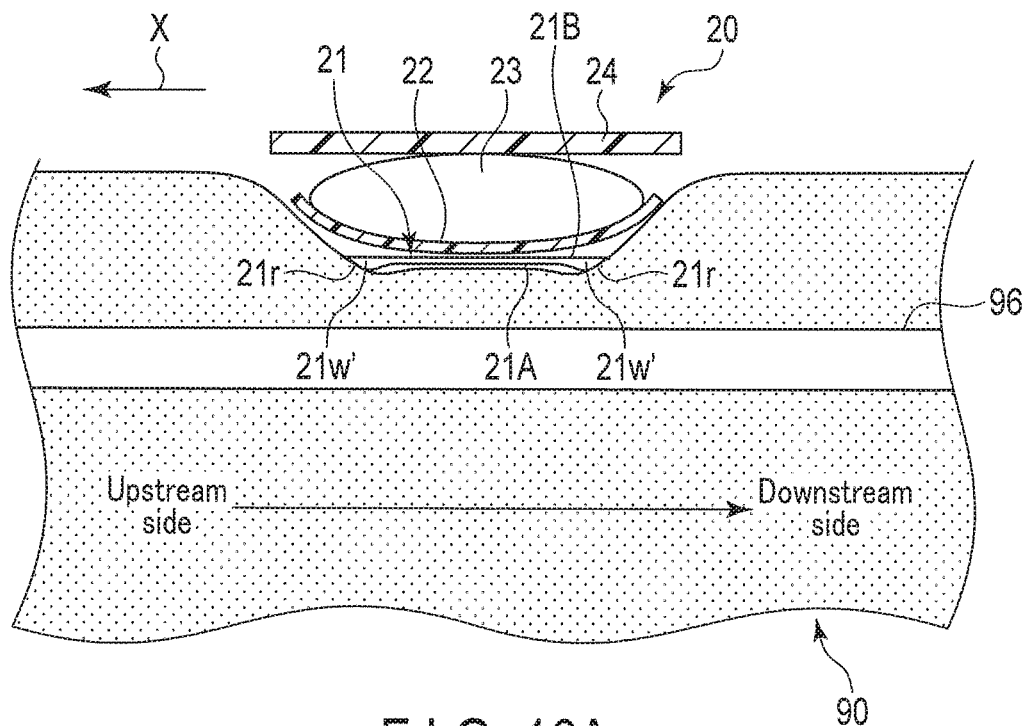
FIG. 16A is a cross-sectional view of a portion of the left wrist in which a tendon extends in a state where the pressure cuff is pressurized.
Figure 16B:
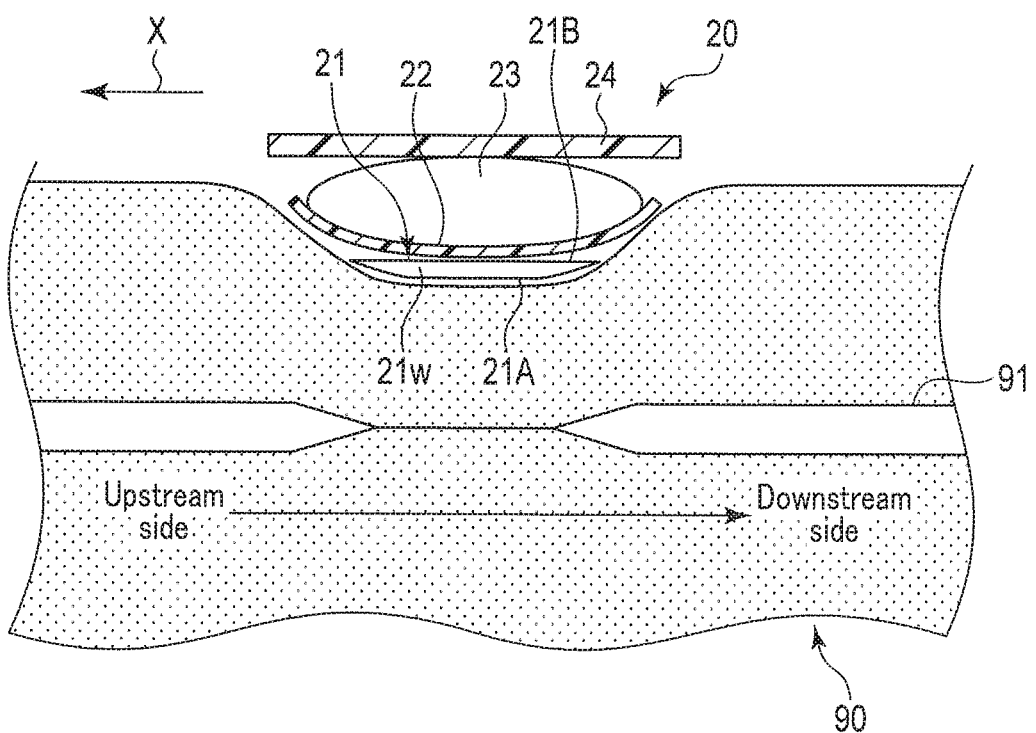
FIG. 16B is a cross-sectional view of a portion of the left wrist in which a radial artery extends in the state where the pressure cuff is pressurized.

FIGS. 16A and 16B are schematic cross-sectional views of the sensing cuff 21 illustrating a pressurization state in which an appropriate amount of air is contained in the sensing cuff 21 with the on-off valve 33 closed, and are taken along the longitudinal direction (corresponding to the width direction X of the cuff) of the left wrist 90. FIG. 16A is a cross-sectional view of a portion of the left wrist 90 involving passage of the tendon 96 (corresponds to a cross-sectional view taken along line XVIA-XVIA in FIG. 14). FIG. 16B is a cross-sectional view of a portion of the left wrist 90 involving passage of the radial artery (corresponds to a cross-sectional view taken along line XVIB-XVIB in FIG. 14).

As illustrated in FIG. 16B, the portion of the left wrist 90 in which the radial artery 91 extends is relatively soft and thus a gap 21w including air remains between the first sheet 21A and the second sheet 21B of the sensing cuff 21. Therefore, the portion of the sensing cuff 21 facing the radial artery 91 can reflect the pressure of the artery-passing portion 90a of the left wrist 90. On the other hand, as illustrated in FIG. 16A, the portion of the left wrist 90 in which the tendon 96 extends is relatively stiff, and thus the first sheet 21A and the second sheet 21B are in contact with each other in a portion corresponding to substantially the center of the sensing cuff 21 in the width direction X. Still, in the sensing cuff 21, the slack 21r extending along the longitudinal direction Y (corresponding to the circumference direction of the left wrist 90) is provided at the portion continuing to the edge portions 21m on both sides in the width direction X as described above, whereby a gap 21w' including air remains along the longitudinal direction Y. As a result, the air in the sensing cuff 21 can flow along the longitudinal direction Y of the sensing cuff 21 through the gap 21w'. Thus, the sensing cuff 21 can sufficiently transmit the pressure, applied to the artery-passing portion 90a of the left wrist 90, to the second pressure sensor 32 in the main body 10 as the pressure of air (a fluid for transmitting pressure).

The CPU 100 acquires the pulse wave signal Pm and the like as described above, and applies a known algorithm according to an oscillometric method based on the pulse wave signal Pm in an attempt to obtain a blood pressure value (systolic blood pressure SBP and diastolic blood pressure DBP) (step S9 of FIG. 12). Next, the CPU 100 performs control to stop the pump 30 and discharge the air in the pressure cuff 23.

Subsequently, the CPU 100 determines whether the blood pressure value has been successfully measured (step S11 of FIG. 12). When the CPU 100 determines NO (for example, when the calculation of the blood pressure value fails due to lack of data), the sequence including steps S9 to S11 is repeated as long as the pressure of the pressure cuff 23 falls below the upper limit pressure (determined to be 300 mmHg for in advance for safety for example). When the CPU 100 determines YES, the CPU 100 performs control to open the on-off valve 33 (step S12 in FIG. 12), so that the air in the sensing cuff 21 is also discharged.

The blood pressure value calculated by the CPU 100 in this manner is stored in the memory 51 as a blood pressure value X0 (step S13 of FIG. 12). The CPU 100 controls the operation of the display 50 so that the blood pressure value X0 is displayed (step S14 of FIG. 12).

In this example, steps S1 and S2 are performed before step S3, but step S1 may be performed after step S3 and before step S4, and step S2 may be performed after step S3 and before step S6.

With the blood pressure monitor 1, it is possible to achieve high blood pressure measurement accuracy while employing a double cuff structure. This will be described below.

As illustrated in FIG. 14, in the mounted state, the sensing cuff 21 is in close contact with the outer circumference surface of the left wrist 90. In this state, the sensing cuff 21 can be roughly divided into five regions. These five regions include a region F1 corresponding to the ulna 94, a region F2 corresponding to the ulnar artery 92, a region F3 corresponding to the tendon, a region F4 corresponding to the radial artery 91, and a region F5 corresponding the radius 93, as indicated by dotted-line ovals in FIG. 14. Among these regions, the region F1 corresponding to the ulna 94, the region F3 corresponding to the tendon, and the region F4 corresponding to the radial artery 91 are regions, in the measurement site, respectively including the ulna 94, tendon 96, and the radius 93 and thus correspond to rigid parts. The region F2 corresponding to the ulnar artery 92 and the region F4 corresponding to the radial artery 91 are regions, in the measurement site, respectively including the ulnar artery 92 and the radial artery 91 and thus correspond to soft parts.

If the sensing cuff 21 is pressed against the wrist in a state where the fluid is contained in an amount large enough for inflating the sensing cuff 21 in all of the region F1, the region F2, the region F3, the region F4, and the region F5, the blood pressure value is calculated with the second pressure sensor 32 detecting the repulsive force from all the regions as the internal pressure of the sensing cuff 21. However, since the regions F1, F3 and F5 are regions respectively including the ulna 94, the tendon 96, and the radius 93 and thus correspond to the rigid parts, the repulsive force from these rigid parts against the pressing force is larger than that from the soft parts in the vicinity of the ulnar artery 92 and the radial artery 91. As a result, the internal pressure of the sensing cuff 21 as a whole will be higher than the pressure in the vicinity of the ulnar artery 92 and the radial artery 91, resulting in a larger error in the blood pressure value. The amount of fluid contained in the sensing cuff 21 is also related to the generation of tension on the first sheet 21A and the second sheet 21B forming the sensing cuff 21. Specifically, the tension increases and the internal pressure of the sensing cuff 21 rises as the amount of fluid increases. Thus, such a case also involves a large error in the blood pressure value. As described above, when the fluid is contained in the region F1, the region F3, and the region F5, the internal pressure is increased due to the influence of the repulsive force and the tension, resulting in a large error in the blood pressure value.

Still, the fluid may be supplied in a state illustrated in FIG. 14 to be free of the above-described influence of the rigid parts. Specifically, in this state, the first sheet 21A and the second sheet 21B are in contact with each other in the regions F1, F3 and F5, the first sheet 21A and the second sheet 21B are spaced apart from each other in the regions F2 and F4. Thus, when the sensing cuff 21 is pressed against the wrist with such an amount of fluid, the fluid does not exist in the region F1, the region F3, and the region F5 corresponding to the rigid parts described above (the fluid could exist in these regions but will escape therefrom), and is accommodated in the regions F2 and F4 corresponding to the respective two arteries which are the radial artery 91 and the ulnar artery 92. Furthermore, in this blood pressure monitor 1, the sensing cuff 21 includes the slack 21r extending along the longitudinal direction Y (corresponding to the circumference direction of the left wrist 90) at the portion continuous with the edge portions 21m on both sides in the width direction X as illustrated in FIG. 16A, whereby the gap 21w' remains along the longitudinal direction Y. As a result, the fluid accommodated in the regions F1, F3 and F5 in the sensing cuff 21, flows through the gap 21w to the regions F2 and F3, to be stored in the regions F2 and F3. Although the first sheet 21A and the second sheet 21B are illustrated to be slightly spaced apart from each other in FIG. 16A for the sake of easy understanding, the first sheet 21A and the second sheet 21B are actually in contact with each other.

Thus, with the amount of fluid as illustrated in FIG. 14, the regions F1, F3, and F5 do not include the fluid, whereby the repulsive force from the ulna 94, the tendon 96, and the radius 93 does not contribute to the internal pressure of the sensing cuff 21. Furthermore, due to the absence of the fluid, tension due to the fluid is not generated in the first sheet 21A and the second sheet 21B in these regions.

On the other hand, in the regions F2 and F4 that include the two respective arteries, which are the radial artery 91 and the ulnar artery 92, and thus correspond to the soft parts, the fluid is contained until the first sheet 21A and the second sheet 21B of the sensing cuff 21 are spaced apart from each other. Therefore, the pressure around the radial artery 91 and the ulnar artery 92 is detected as the internal pressure of the sensing cuff 21. As described above, by setting the amount of fluid to be the amount as illustrated in FIG. 14, the internal pressure of the sensing cuff 21 is mainly detected from the regions F2 and F4 that include the two respective arteries, which are the radial artery 91 and the ulnar artery 92, and correspond to the soft parts. Thus, the internal pressure of the sensing cuff 21 and the pressure around the radial artery 91 and the ulnar artery 92 can be equalized, whereby the error in the blood pressure value should be small.

However, as described above, the positions of the arteries and bones and the amount of fat at the measurement site of the subject, which is the wrist, the ankle, or the upper arm for example vary among individuals. Furthermore, the blood pressure value of the subject also varies among individuals. The differences in the positions of the artery and bone, the amount of fat, and the blood pressure value, lead to differences in how the pulse wave signal is transmitted, making it difficult to achieve high blood pressure measurement accuracy.

As described above, the blood pressure monitor 1 determines the amount of the second fluid to be supplied to the sensing cuff 21 based on the biometric information about the subject. The height, the weight, the body fat percentage, the circumference length of the measurement site, and the like are somewhat correlated with the positions of the artery and bone and the amount of fat. Therefore, high blood pressure measurement can be performed with the amount of fluid in the sensing cuff set according to biometric information such as blood pressure value, height, body weight, body fat percentage, and circumference length of the measurement site, so that high blood pressure measurement accuracy can be achieved. Thus, with the blood pressure monitor 1, it is possible to achieve high blood pressure measurement accuracy while employing a double cuff structure.

Furthermore, the blood pressure monitor 1 uses biometric information known in advance. Therefore, high blood pressure measurement accuracy can be achieved from the blood pressure measurement performed for the first time.

Furthermore, as described above, in the blood pressure monitor 1, the air serving as the second fluid is supplied to the sensing cuff 21 each time the blood pressure is measured, and the second pressure sensor 32 detects the pressure Pc of the sensing cuff 21 independently from the pressure cuff 23, whereby the pressure of the artery-passing portion 90a of the left wrist 90 is directly detected. Therefore, the blood pressure value can be accurately measured, even when the pressure loss occurs due to a large inflation of the pressure cuff 23 in the thickness direction at the time of pressurization as a result of setting the dimension of the belt 2 and the cuff structure 20 (hereinafter, also simply referred to as "cuff" as appropriate) in the width direction X short (about 25 mm for example).

Furthermore, in the mounted state, the sensing cuff 21 extends in the circumference direction Y over the artery-passing portion 90a of the left wrist 90. Therefore, when the subject actually mounts the blood pressure monitor 1 on the left wrist 90, even if the cuff along with the main body 10 is somewhat displaced in the circumference direction Y of the left wrist 90, the sensing cuff 21 is not displaced from the artery-passing portion 90a of the left wrist 90. Therefore, it is possible to prevent the blood pressure measurement value from deviating from the actual blood pressure, and thus the blood pressure value can be measured accurately.

First Modification of Blood Pressure Measurement Method

The blood pressure monitor 1 described above may be capable of switching a measurement mode from a first mode to a second mode, perform measurement in the first mode with the method described with reference to FIGS. 11 and 12, and perform measurement in the second mode with a method illustrated in FIG. 15.

Figure 15:
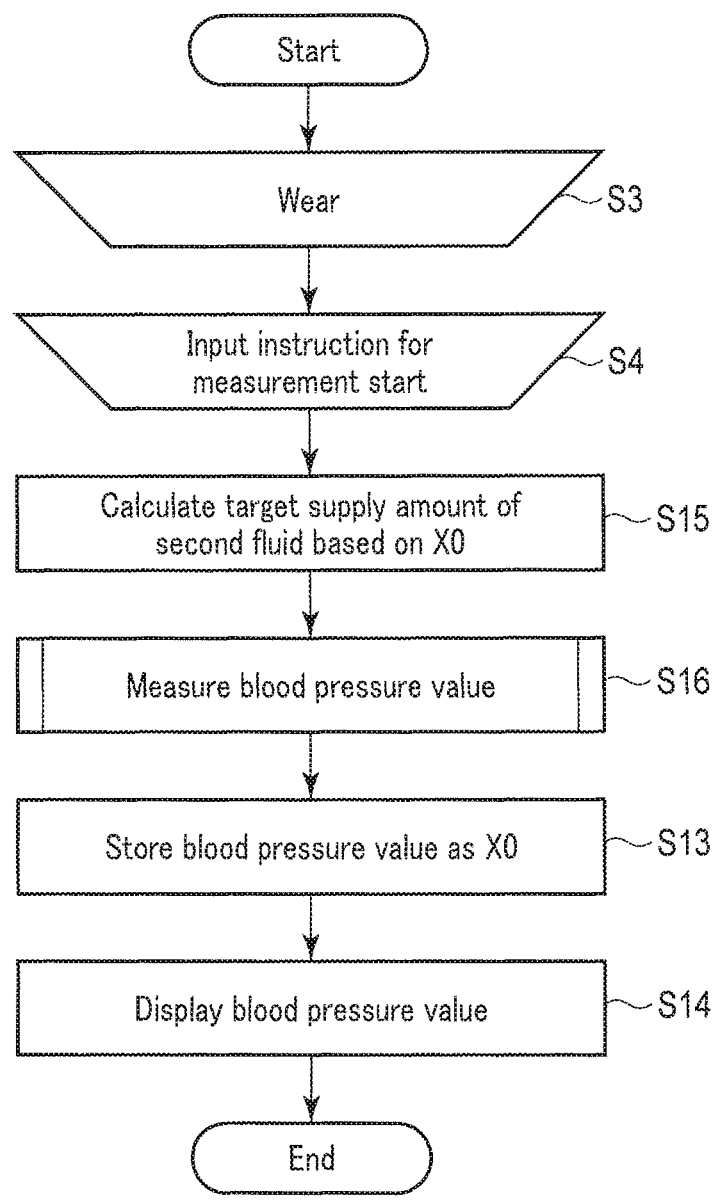
FIG. 15 is a flowchart illustrating a blood pressure measurement method performed after the blood pressure value has been measured by the method illustrated in FIGS. 11 and 12.

FIG. 15 is a flowchart illustrating a blood pressure measurement method performed after the blood pressure value has been measured by the method illustrated in FIGS. 11 and 12.

In this method, first of all, steps S3 and S4 described with reference to FIG. 11 are sequentially performed. Next, the amount of the second fluid to be supplied to the sensing cuff 21, that is, the target supply amount is calculated based on the blood pressure value X0 stored in the memory 51 in step S13 described with reference to FIG. 12 (step S15 of FIG. 15). Specifically, the target supply amount is calculated from this blood pressure value X0 and the above-mentioned relational expression or table stored in the memory 51. The memory 51 stores this target supply amount.

Next, the CPU 100 performs the control described with reference to steps S5 to S12 in FIGS. 11 and 12. Thus, the blood pressure value is measured (step S16 of FIG. 15).

The blood pressure value calculated by the CPU 100 in this manner is stored in the memory 51 as a blood pressure value X0 (step S13 of FIG. 15). In other words, the blood pressure value X0 is overwritten. The CPU 100 controls the operation of the display 50 so that the blood pressure value X0 is displayed (step S14 of FIG. 15).

A subject's blood pressure value is not always constant. For example, the blood pressure of the subject at the time of blood pressure measurement may be deviated from the blood pressure value input to the blood pressure monitor 1 by the subject. If the deviation of the blood pressure value is small, high blood pressure measurement accuracy can be achieved, but if this deviation becomes large, it becomes difficult to achieve high blood pressure measurement accuracy. Therefore, for example, the measurement according to the method described with reference to FIGS. 11 and 12, that is, the measurement according to the first mode is performed when the monitor is used for the first time. Then, the method described with reference to FIG. 15, that is, the measurement in the second mode is performed when the monitor is used for the second time and after. Thus, the blood pressure measurement can be constantly performed with high accuracy, even when the blood pressure value of the subject gradually changes.

Second Modification of Blood Pressure Measurement Method

Figure 18:
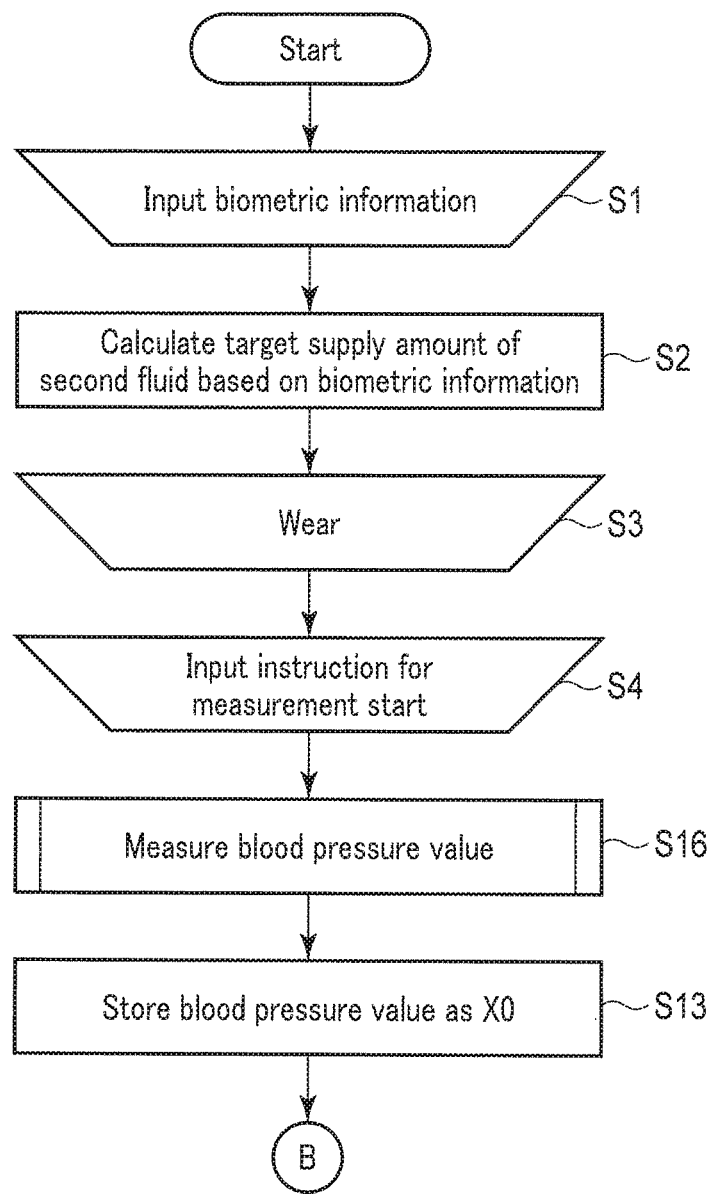
FIG. 18 is a flowchart illustrating some steps of a blood pressure measurement method according to another example.
Figure 19:
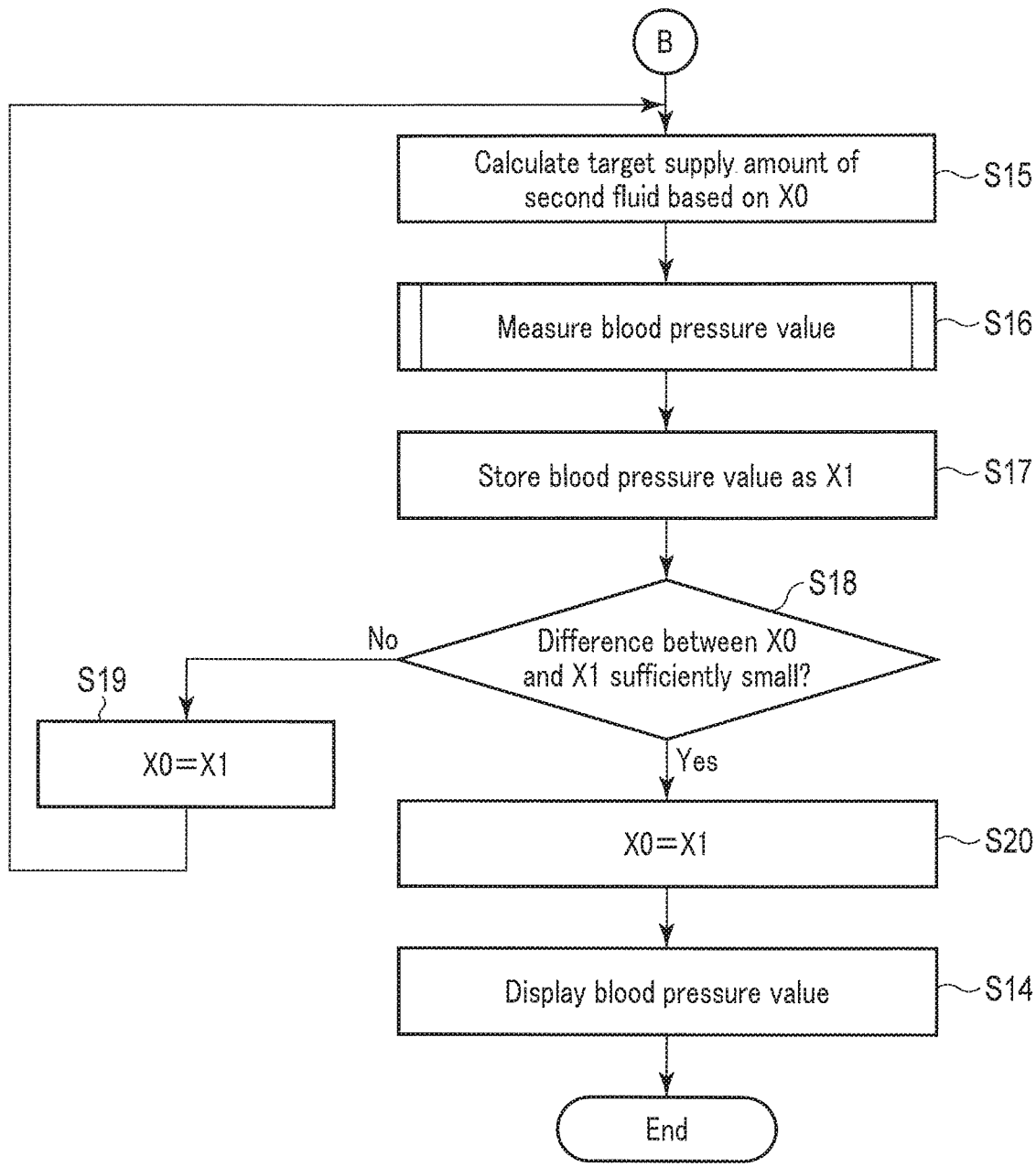
FIG. 19 is a flowchart illustrating the remaining steps of the blood pressure measurement method the some steps of which are illustrated in FIG. 18.

FIG. 18 is a flowchart illustrating some steps of a blood pressure measurement method according to another example. FIG. 19 is a flowchart illustrating the remaining steps of the blood pressure measurement method the some steps of which are illustrated in FIG. 18.

In this method, first of all, steps S1 to S13 described with reference to FIGS. 11 and 12 are sequentially performed, as illustrated in FIG. 18. Step S16 of FIG. 18 corresponds to steps S5 to S12 of FIGS. 11 and 12.

Next, as illustrated in FIG. 19, the amount of the second fluid to be supplied to the sensing cuff 21, that is, the target supply amount is calculated based on the blood pressure value X0 stored in the memory 51 in step S13 of FIG. 18 (step S15 of FIG. 15). Specifically, the target supply amount is calculated from this blood pressure value X0 and the above-mentioned relational expression or table stored in the memory 51. The memory 51 stores this target supply amount.

Next, the blood pressure value is measured as in step S16 of FIG. 18 (step S16 of FIG. 19). The blood pressure value calculated by the CPU 100 in this manner is stored in the memory 51 as a blood pressure value X1 (step S17 of FIG. 19).

Next, the CPU 100 determines whether the difference between the blood pressure value X0 and the blood pressure value X1 is sufficiently small (step S18 of FIG. 19). Specifically, the CPU 100 determines whether the difference between the blood pressure value X0 and the blood pressure value X1 is within a predetermined tolerable range.

When the CPU 100 determines NO, the blood pressure value X1 is stored in the memory 51 as the blood pressure value X0. That is, the blood pressure value X0 is overwritten with the blood pressure value X1 (step S19 of FIG. 19). Then, the CPU 100 performs steps S15 to S18 of FIG. 19 again.

Also when the CPU 100 determines YES, the blood pressure value X1 is stored in the memory 51 as the blood pressure value X0. That is, the blood pressure value X0 is overwritten with the blood pressure value X1 (step S20 of FIG. 19). The CPU 100 controls the operation of the display 50 so that the blood pressure value X0 is displayed (step S14 of FIG. 19).

The blood pressure value varies according to the physical condition of the subject, the measurement time, and the like. With the blood pressure monitor 1 employing the above blood pressure measurement method, high blood pressure measurement accuracy can be achieved even when the blood pressure value largely fluctuates in a short period of time.

Third Modification of Blood Pressure Measurement Method

The blood pressure measurement method described with reference to FIGS. 18 and 19 may be combined with a blood pressure measurement method illustrated in FIG. 20.

Figure 20:
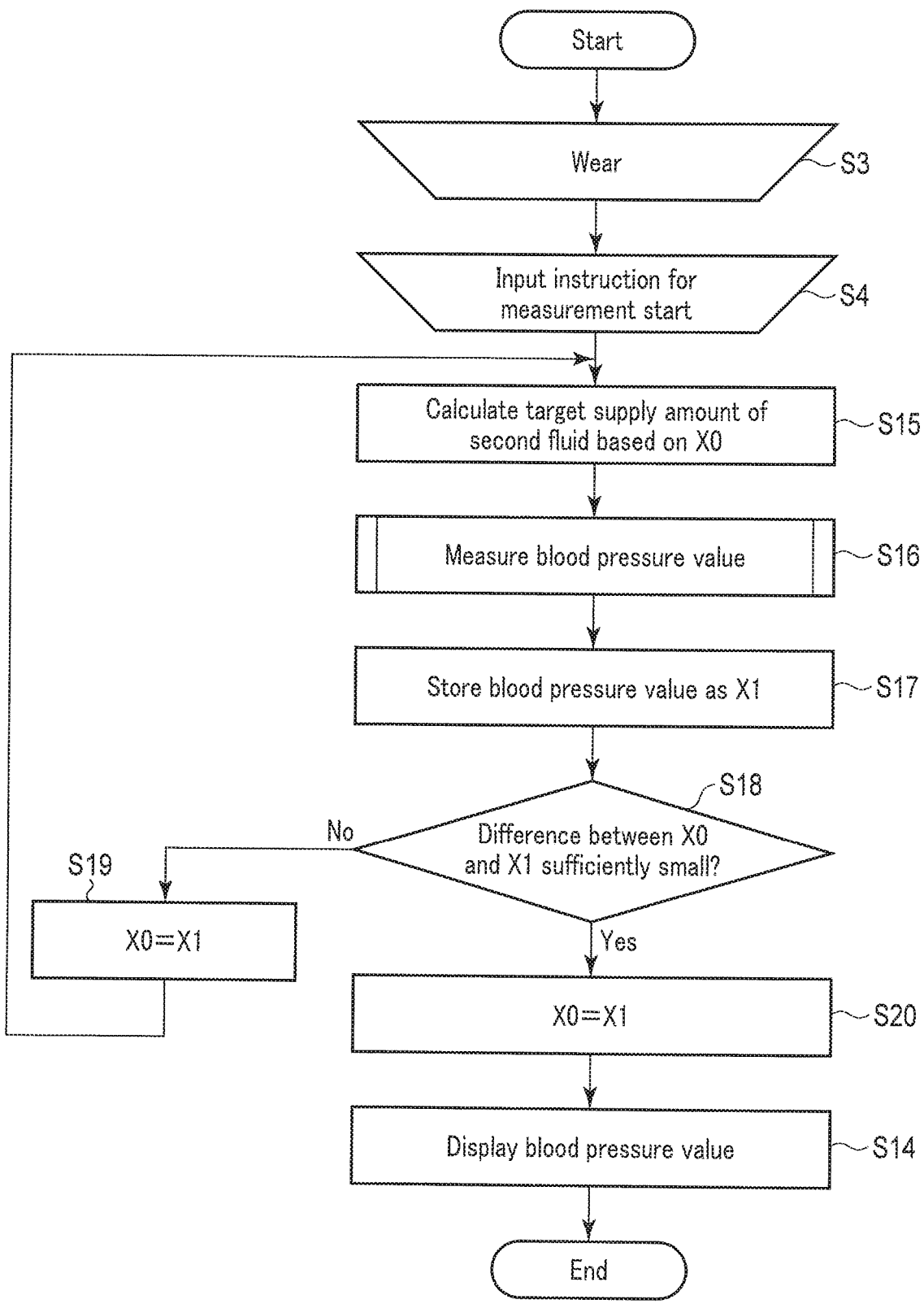
FIG. 20 is a flowchart illustrating a blood pressure measurement method performed after the blood pressure value has been measured by the method illustrated in FIGS. 18 and 19.

FIG. 20 is a flowchart illustrating a blood pressure measurement method performed after the blood pressure value has been measured by the method illustrated in FIGS. 18 and 19.

The blood pressure measurement method described with reference to FIGS. 18 and 19 is combined with the blood pressure measurement method illustrated in FIG. 20 in such a manner that the measurement by the former is performed as the measurement in the first mode and the measurement by the latter is performed as the measurement in the second mode. The blood pressure monitor 1 described above is assumed to be capable of switching the measurement mode from the first mode to the second mode.

In the measurement in the second mode, that is, in the measurement by the method illustrated in FIG. 20, steps S3 and S4 described with reference to FIG. 18 are sequentially performed. Next, steps S15 to S18 described with reference to FIG. 19 are sequentially performed.

When the CPU 100 determines NO, the blood pressure value X1 is stored in the memory 51 as the blood pressure value X0. That is, the blood pressure value X0 is overwritten with the blood pressure value X1 (step S19 of FIG. 20). Then, the CPU 100 performs steps S15 to S18 of FIG. 20 again.

Also when the CPU 100 determines YES, the blood pressure value X1 is stored in the memory 51 as the blood pressure value X0. That is, the blood pressure value X0 is overwritten with the blood pressure value X1 (step S20 in FIG. 20). The CPU 100 controls the operation of the display 50 so that the blood pressure value X0 is displayed (step S14 of FIG. 20).

With the blood pressure monitor 1 employing the above blood pressure measurement method, high blood pressure measurement accuracy can be achieved even when the blood pressure value largely fluctuates in a short period of time. Further, for example, in the case where the measurement according to the method described with reference to FIGS. 18 and 19, that is, the measurement in the first mode is performed when the monitor is used for the first time, and the measurement according to the method described with reference to FIG. 20, that is, the measurement in the second mode is performed when the monitor is used for the second time and after, the difference between the blood pressure value X0 and the blood pressure value X1 can be made sufficiently small with a relatively small number of times, even when the blood pressure value of the subject gradually changes.

Fourth Modification of Blood Pressure Measurement Method

Figure 21:
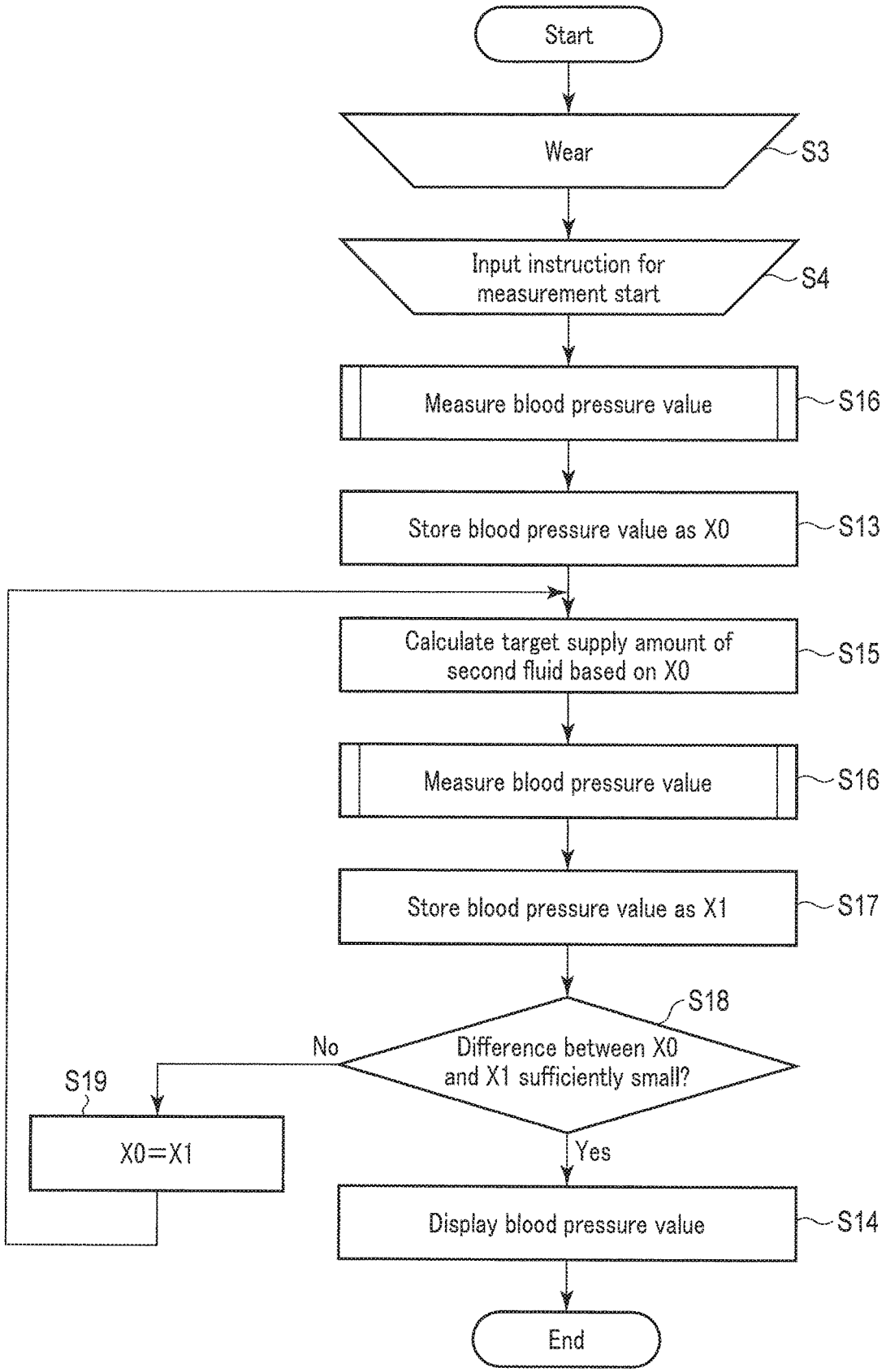
FIG. 21 is a flowchart illustrating a blood pressure measurement method according to still another example.

FIG. 21 is a flowchart illustrating a blood pressure measurement method according to still another example.

This method is the same as that described with reference to FIG. 18 and FIG. 19 except that steps S1, S2, and S20 are omitted, with the target supply amount of the second fluid to be used in the first measurement stored in advance in the memory 51.

With the blood pressure monitor 1 employing the above blood pressure measurement method, high blood pressure measurement accuracy can be achieved even when the blood pressure value largely fluctuates in a short period of time. Such a blood pressure monitor 1 does not require the subject to input biometric information, and thus can be simply operated.

Other Modifications

The above blood pressure monitor 1 may be mounted for a long period of time, and blood pressure measurement may be repeated at short time intervals. Alternatively, blood pressure measurements may be repeated at relatively long time intervals. Still, the blood pressure value varies among time zones. For example, the variation in blood pressure value is large at night. Therefore, when the method described with reference to FIGS. 11 and 12 or the method described with reference to FIG. 15 is employed, for example, the blood pressure value measured in the time zone where the variation in blood pressure value is large is preferably not used for determining the target supply amount of the second fluid. Alternatively, in this case, the average of blood pressure values obtained through a plurality of measurements is preferably used to determine the target supply amount of the second fluid.

The material of the sensing cuff 21 may not be silicone resin. For example, the material of the sensing cuff 21 may be a thermoplastic elastomer such as a thermoplastic polyurethane. The material of the sensing cuff 21 may be elastomer of any of rubber, thermoplastic resin, and thermosetting resin.

The sensing cuff 21 preferably has a Shore A hardness of 60 or less. The sensing cuff 21 having a high Shore A hardness involves a large variation in tension due to a change in the amount of the second fluid supplied thereto. Therefore, when such a sensing cuff 21 is used, it is difficult to set the tension finely. On the other hand, the sensing cuff 21 having a low Shore A hardness involves a small variation in tension due to a change in the amount of the second fluid supplied thereto. That is, when such a sensing cuff 21 is used, the tension thereof can be set more finely, and therefore, blood pressure measurement with high accuracy can be easily achieved.

The sensing cuff 21 preferably has a Shore A hardness of 10 or more. When the Shore A hardness is too low, introduction of the fluid into the sensing cuff 21 is likely to lead to local inflation, making it difficult to achieve uniform tension of the sensing cuff 21. As a result, the blood pressure measurement accuracy is degraded.

While the blood pressure monitor 1 described above acquires the pulse wave signal Pm in the process of pressurizing the pressure cuff 23, the pulse wave signal Pm may also be acquired in the process of reducing the pressure of the pressure cuff 23.

The first and second fluids may not be air. For example, at least one of the first and the second fluids may be a liquid, such as water.

The above-described blood pressure monitor 1 may be a blood pressure measurement apparatus further having other functions, such as a clock function, in addition to the blood pressure measurement function. For example, the blood pressure monitor 1 described above may be a smart watch having a blood pressure measurement function.

Although the above-described blood pressure monitor 1 is attached to the wrist, the above-described technique is also applicable to a blood pressure monitor attached to another measurement site such as an ankle and an upper arm.

EXAMPLES

Examples of the present invention are described below.

Test 1

Blood pressure measurement was performed on each of four subjects (monitoring targets) A to D using the blood pressure monitor 1 described above.

Specifically, the subjects A and B were tested with the blood pressure monitor 1 in which the sensing cuff 21 and the pressure cuff 23 are made of thermoplastic polyurethane having a Shore A hardness of 75. The subjects C and D were tested with the blood pressure monitor 1 similar to that used for subjects A and B except that the sensing cuff 21 was made of silicone resin having a Shore A hardness of 30. Then, for each of the subjects A to D blood pressure measurement was performed multiple times with the amount of air supplied to the sensing cuff 21 changed. The results are illustrated in FIG. 22 and FIG. 23.

Figure 22:
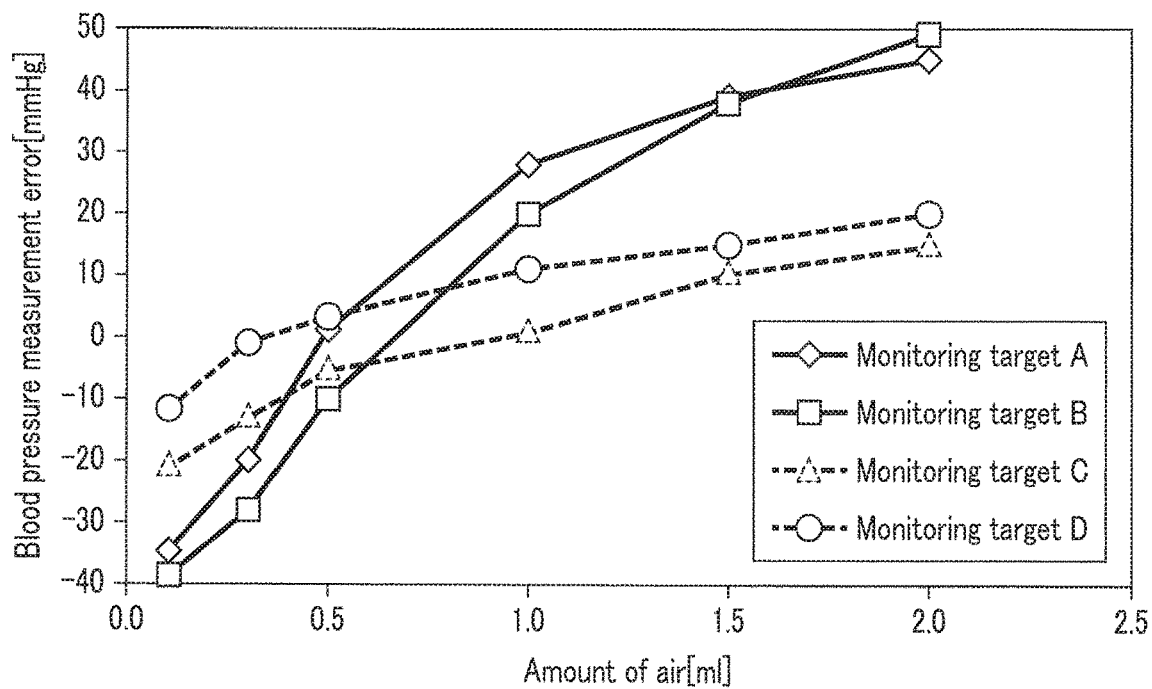
FIG. 22 is a graph showing an example of the relationship between the amount of air to the sensing cuff and a blood pressure measurement error.

FIG. 22 is a graph showing an example of the relationship between the amount of air to the sensing cuff and a blood pressure measurement error. FIG. 23 is a graph depicting a part of FIG. 22 in an enlarged manner.

Here, the blood pressure measurement error is a difference as a result of subtracting a blood pressure value (systolic blood pressure SBP) measured by a standard (accurate) blood pressure monitor (this will be referred to as a "reference blood pressure value") from a blood pressure value (systolic blood pressure SBP) measured by the blood pressure monitor 1 for a subject. Thus, (blood pressure measurement error)=(blood pressure value measured by blood pressure monitor 1)−(reference blood pressure value) holds true.

Figure 23:
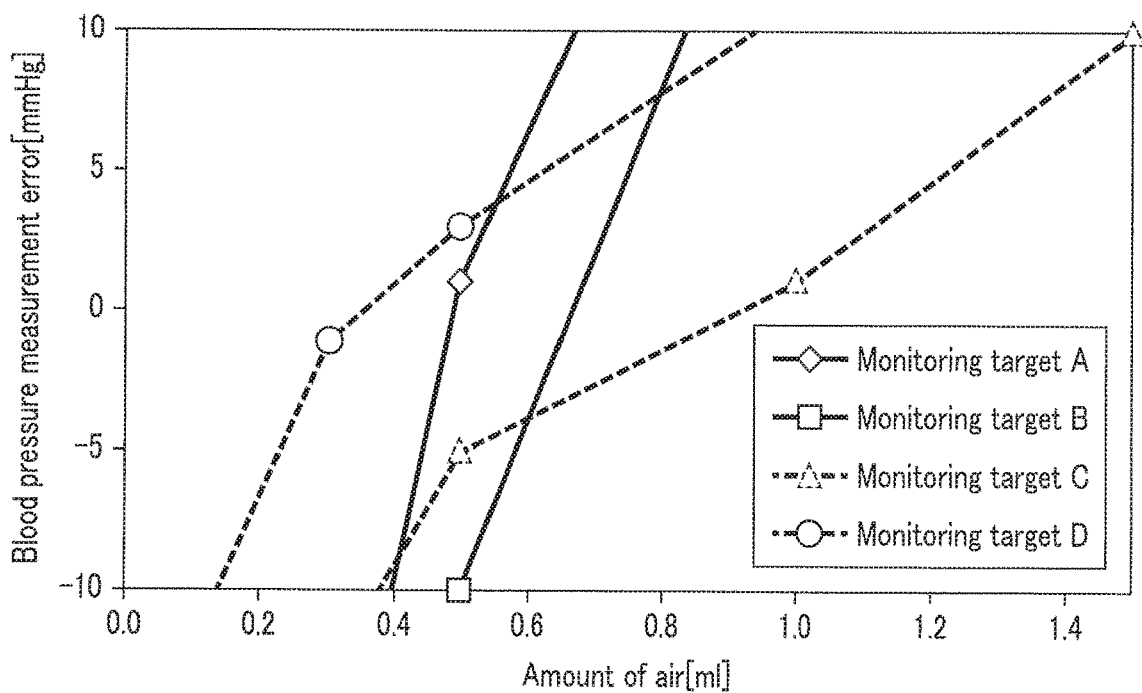
FIG. 23 is a graph depicting a part of FIG. 22 in an enlarged manner.

As illustrated in FIGS. 22 and 23, the air amount of the sensing cuff and the blood pressure measurement error are correlated. In a case that the silicone resin having a Shore A hardness of 30 is used as the material of the sensing cuff 21, the amount of air supplied to the sensing cuff 21 has a smaller impact on the blood pressure measurement accuracy, compared with a case that the thermoplastic elastomer having a Shore A hardness of 75 is used as the material of the sensing cuff 21.

Test 2

Blood pressure measurement was performed on each of the 12 subjects using the blood pressure monitor 1 described above.

Specifically, all the subjects A and B were tested with the blood pressure monitor 1 in which the pressure cuff 23 is made of thermoplastic polyurethane having a Shore A hardness of 75 and the sensing cuff 21 made of silicone resin having a Shore A hardness of 30. Then, as in Test 1, the blood pressure measurement was performed multiple times with the amount of air supplied to the sensing cuff 21 changed. Then, the amount of air achieving the blood pressure measurement error of 0 mmHg was obtained. The results are illustrated in FIGS. 24 and 25.

FIG. 24 is a graph showing an example of the relationship between the reference blood pressure value and the amount of air in the sensing cuff. FIG. 25 is a graph showing an example of the relationship between the circumference length of the measurement site and the amount of air in the sensing cuff.

As illustrated in FIG. 24, the reference blood pressure value and the amount of air in the sensing cuff are highly correlated. Furthermore, as illustrated in FIG. 25, the circumference length of the measurement site and the amount of air in the sensing cuff are also highly correlated.

Test 3

Blood pressure measurement was performed on each of the 12 subjects using the blood pressure monitor 1 described above.

Specifically, all subjects A and B were tested with the blood pressure monitor 1 that is the same as that used in Test 2. Then, for each subject, the amount of air supplied to the sensing cuff 21 was determined from the reference blood pressure value of the subject and the graph illustrated in FIG. 24. The blood pressure measurement was performed with the amount of air thus determined. Furthermore, for each subject, blood pressure measurement was performed with the amount of air supplied to the sensing cuff 21 set to be 0.5 mL. Furthermore, for each subject, blood pressure measurement was performed with the amount of air supplied to the sensing cuff 21 set to be 1.0 mL. The results are illustrated in FIG. 26.

As illustrated in FIG. 26, with the amount (fluid amount) of air supplied to the sensing cuff 21 individually set, the blood pressure measurement error was able to be largely reduced from that in a case that the fluid amount is fixed at 0.5 mL or 1.0 mL.

The invention claimed is:

1. A blood pressure monitor comprising:
a pressing member that includes a pressure cuff having a bag shape capable of containing a first fluid and generates a pressing force toward a measurement site of a subject when the pressing member is wound around the measurement site and the pressure cuff is inflated;
a sensing cuff having a bag shape capable of containing a second fluid and provided on a facing surface of the pressing member that faces the measurement site;
an adjuster that adjusts an amount of the first fluid in the pressure cuff and an amount of the second fluid in the sensing cuff;
a pressure sensor that detects pressure in the sensing cuff; and
a controller that controls an operation of the adjuster such that the second fluid is contained in the sensing cuff in an amount corresponding to biometric information about the subject and the pressure cuff is inflated or inflated and deflated in this state when performing a blood pressure measurement, and calculates a blood pressure value of the subject based on an output from the pressure sensor,
wherein the pressure cuff includes two fluid bags each having first and second opposing welded edge portions in a width direction and stacked in a thickness direction, and the fluid bags are provided with through holes such that the first fluid flows from one of the fluid bags through the through holes into the other of the fluid bags, and
wherein the sensing cuff has a single bag structure and includes a first sheet facing the facing surface, and a second sheet positioned between the first sheet and the facing surface, the first sheet and the second sheet are formed to have a bag shape with their circumference edge portions welded to each other, a portion of the sensing cuff excluding the circumference edge portions has a length in a width direction of the sensing cuff smaller than a length of a portion of the pressure cuff excluding the welded edge portions in the width direction, and the sensing cuff in a natural state with one of the first sheet and the second sheet being flat has a slack in the other of the first sheet and the second sheet, the slack extending along a longitudinal direction of the sensing cuff between edges on both ends in the width direction of the sensing cuff; and
a back plate between the pressure cuff and the sensing cuff, the back plate extending lengthwise along a circumference direction of the measurement site, the back plate having a width spanning only the portion of the pressure cuff excluding the first and second welded edge portions and the width of the back plate being wider than a width of the sensing cuff.

2. The blood pressure monitor according to claim 1, further comprising an input unit for inputting information, wherein
the input unit includes at least one of a push-type switch, a touch-type input apparatus, an audio-based input apparatus provided with a microphone, and a communication-based input apparatus for wired or wireless communication, and
the controller controls the operation of the adjuster using at least part of the information input through the input unit, as the biometric information, and calculates the blood pressure value of the subject based on the output from the pressure sensor.

3. The blood pressure monitor according to claim 2, wherein the information input through the input unit includes at least one of a blood pressure of the subject and a circumference length of the measurement site.

4. The blood pressure monitor according to claim 1, further comprising an input unit used for inputting information, wherein
the input unit includes at least one of a push-type switch, a touch-type input apparatus, an audio-based input apparatus provided with a microphone, and a communication-based input apparatus for wired or wireless communication, and
the controller is capable of switching a measurement mode from a first mode to a second mode,
when blood pressure measurement is performed in the first mode, the controller controls the operation of the adjuster using, as the biometric information, at least part of the information input through the input unit and calculates the blood pressure value of the subject based on the output from the pressure sensor, and
when the blood pressure measurement is performed in the second mode, the controller controls the operation of the adjuster using, as the biometric information, the blood pressure value calculated by the controller in the blood pressure measurement previously performed, and calculates the blood pressure value of the subject based on the output from the pressure sensor.

5. The blood pressure monitor according to claim 4, wherein the controller repeats the blood pressure measurement in the second mode until variation in the blood pressure value calculated falls within a tolerable range.

6. The blood pressure monitor according to claim 4, wherein the information input through the input unit includes at least one of a blood pressure of the subject and a circumference length of the measurement site.

7. The blood pressure monitor according to claim 1, wherein the controller repeats blood pressure measurement until variation in the blood pressure calculated falls within a tolerable range, and in the blood pressure measurement performed for second time and after, controls an amount of the second fluid supplied to the sensing cuff by the adjuster using, as the biometric information, the blood pressure value calculated by the controller in the blood pressure measurement previously performed.

8. The blood pressure monitor according to a claim 1, wherein the pressing member further includes
a belt that is provided to face an outer circumference surface of the pressure cuff and is wound around the measurement site.

9. The blood pressure monitor according to claim 1, wherein the sensing cuff has a Shore A hardness of 60 or less.

10. The blood pressure monitor according to claim 1, wherein the sensing cuff is located at a center of the pressure cuff in the width direction.

11. A blood pressure measurement apparatus comprising:
a pressing member that includes a pressure cuff having a bag shape capable of containing a first fluid and generates pressing force toward a measurement site of a subject when the pressing member is wound around the measurement site and the pressure cuff is inflated;
a sensing cuff having a bag shape capable of containing a second fluid and provided on a facing surface of the pressing member that faces the measurement site;
an adjuster that adjusts an amount of the first fluid in the pressure cuff and an amount of the second fluid in the sensing cuff;

a pressure sensor that detects pressure in the sensing cuff; and a controller that controls an operation of the adjuster such that the second fluid is contained in the sensing cuff in an amount corresponding to biometric information about the subject and the pressure cuff is inflated or inflated and deflated in this state when performing a blood pressure measurement, and calculates a blood pressure value of the subject based on an output from the pressure sensor, wherein the pressure cuff includes two fluid bags each having first and second opposing welded edge portions in a width direction and stacked in a thickness direction, and the fluid bags are provided with through holes such that the first fluid flows from one of the fluid bags through the through holes into the other of the fluid bags, wherein the sensing cuff has a single bag structure and includes a first sheet facing the facing surface, and a second sheet positioned between the first sheet and the facing surface, the first sheet and the second sheet are formed to have a bag shape with their circumference edge portions welded to each other, a portion of the sensing cuff excluding the circumference edge portions has a length in a width direction of the sensing cuff smaller than a length of a portion of the pressure cuff excluding the welded edge portions in the width direction, and the sensing cuff in a natural state with one of the first sheet and the second sheet being flat has a slack in the other of the first sheet and the second sheet, the slack extending along a longitudinal direction of the sensing cuff between edges on both ends in the width direction of the sensing cuff; and a back plate between the pressure cuff and the sensing cuff, the back plate extending lengthwise along a circumference direction of the measurement site, the back plate having a width spanning only the portion of the pressure cuff excluding the first and second welded edge portions and the width of the back plate being wider than a width of the sensing cuff.

12. The blood pressure measurement apparatus of claim 11, wherein the sensing cuff is located at a center of the pressure cuff in the width direction.

13. A blood pressure measurement method comprising:

winding a pressing member and a sensing cuff around a measurement site of a subject, wherein the pressing member includes a pressure cuff having a bag shape capable of containing a first fluid and generates pressing force toward the measurement site when the pressing member is wound around the measurement site and the pressure cuff is inflated, and the sensing cuff has a bag shape capable of containing a second fluid and is provided on a facing surface of the pressing member that faces the measurement site; and containing the second fluid in the sensing cuff in an amount corresponding to biometric information about the subject, inflating or inflating and deflating the pressure cuff in this state, and obtaining a blood pressure value of the subject based on pressure in the sensing cuff, with the pressure cuff inflated or inflated and deflated in a state that the second fluid in an amount corresponding to biometric information about the subject is contained in the sensing cuff, wherein the pressure cuff includes two fluid bags each having first and second opposing welded edge portions in a width direction and stacked in a thickness direction, and the fluid bags are provided with through holes such that the first fluid flows from one of the fluid bags through the through holes into the other of the fluid bags, wherein the sensing cuff has a single bag structure and includes a first sheet facing the facing surface, and a second sheet positioned between the first sheet and the facing surface, the first sheet and the second sheet are formed to have a bag shape with their circumference edge portions welded to each other, a portion of the sensing cuff excluding the circumference edge portions has a length in a width direction of the sensing cuff smaller than a length of a portion of the pressure cuff excluding the welded edge portions in the width direction, and the sensing cuff in a natural state with one of the first sheet and the second sheet being flat has a slack in the other of the first sheet and the second sheet, the slack extending along a longitudinal direction of the sensing cuff between edges on both ends in a width direction of the sensing cuff; and wherein a back plate is provided between the pressure cuff and the sensing cuff, the back plate extending lengthwise along a circumference direction of the measurement site, the back plate having a width spanning only the portion of the pressure cuff excluding the first and second welded edge portions and the width of the back plate being wider than a width of the sensing cuff.

14. The blood pressure measurement method of claim 13, wherein the sensing cuff is located at a center of the pressure cuff in the width direction.

* * * * *